United States Patent [19]

Mezei, Louis M. et al.

[11] Patent Number: 4,873,633

[45] Date of Patent: Oct. 10, 1989

[54] USER CONTROLLED OFF-CENTER LIGHT ABSORBANCE READING ADJUSTER IN A LIQUID HANDLING AND REACTION SYSTEM

[75] Inventors: Mezei, Louis M., Fremont; Bradley S. Albom, Richmond; Coppock, Stan; Stephen J. Moehle, both of Berkeley; Brent S. Noorda, Pleasant Hill; Joseph T. Widunas, Berkeley; James A. Zeitlin, Piedmont, all of Calif.

[73] Assignee: Cetus Corporation, Emeryville, Calif.

[21] Appl. No.: 906,101

[22] Filed: Sep. 11, 1986

Related U.S. Application Data

[63] Continuation-in-part of Ser. No. 788,998, Oct. 18, 1985, abandoned.

[51] Int. Cl.[4] ............ G01N 33/48; G01N 21/01; G01N 33/80; G01N 35/02
[52] U.S. Cl. .................. 364/413.08; 356/39; 356/442; 422/73
[58] Field of Search .............. 364/416, 555; 422/73; 356/39, 442, 440

[56] References Cited

U.S. PATENT DOCUMENTS

| | | | |
|---|---|---|---|
| 4,130,395 | 12/1978 | Chryssanthou | 424/11 |
| 4,253,846 | 3/1981 | Smythe et al. | 436/53 |
| 4,255,788 | 3/1981 | Schwartz et al. | 364/413.07 |
| 4,268,268 | 5/1981 | Blum | 436/52 |
| 4,319,882 | 3/1982 | Sharma | 436/63 |
| 4,451,433 | 5/1984 | Yamashita et al. | 422/63 |
| 4,478,094 | 10/1984 | Solomaa et al. | 73/863.32 |
| 4,556,641 | 12/1985 | Kano et al. | 422/73 X |
| 4,580,895 | 4/1986 | Patel | 356/39 |
| 4,608,246 | 8/1986 | Bayer et al. | 424/11 |
| 4,665,553 | 5/1987 | Gershman et al. | 356/39 X |
| 4,678,894 | 7/1987 | Shafer | 364/416 X |
| 4,683,120 | 7/1987 | Meserol et al. | 422/72 |
| 4,713,348 | 12/1987 | Ullman | 436/501 |
| 4,719,087 | 1/1988 | Hanaway | 422/102 |
| 4,727,033 | 2/1988 | Hijikata et al. | 356/39 |

*Primary Examiner*—Clark A. Jablon
*Attorney, Agent, or Firm*—Ronald C. Fish; Kevin R. Kaster; Albert P. Halluin

[57] ABSTRACT

A host computer controls a plate reader which optically reads the results between donor samples and reagents. The system provides the user with the ability to change the position of off-center light absorbance readings to maximize the power of the machine to discriminate between positive and negative agglutination reactions. In addition, the user can tailor thresholds for absorbances used to distinguish between positive, negative and "no type determined" reactions.

7 Claims, 4 Drawing Sheets

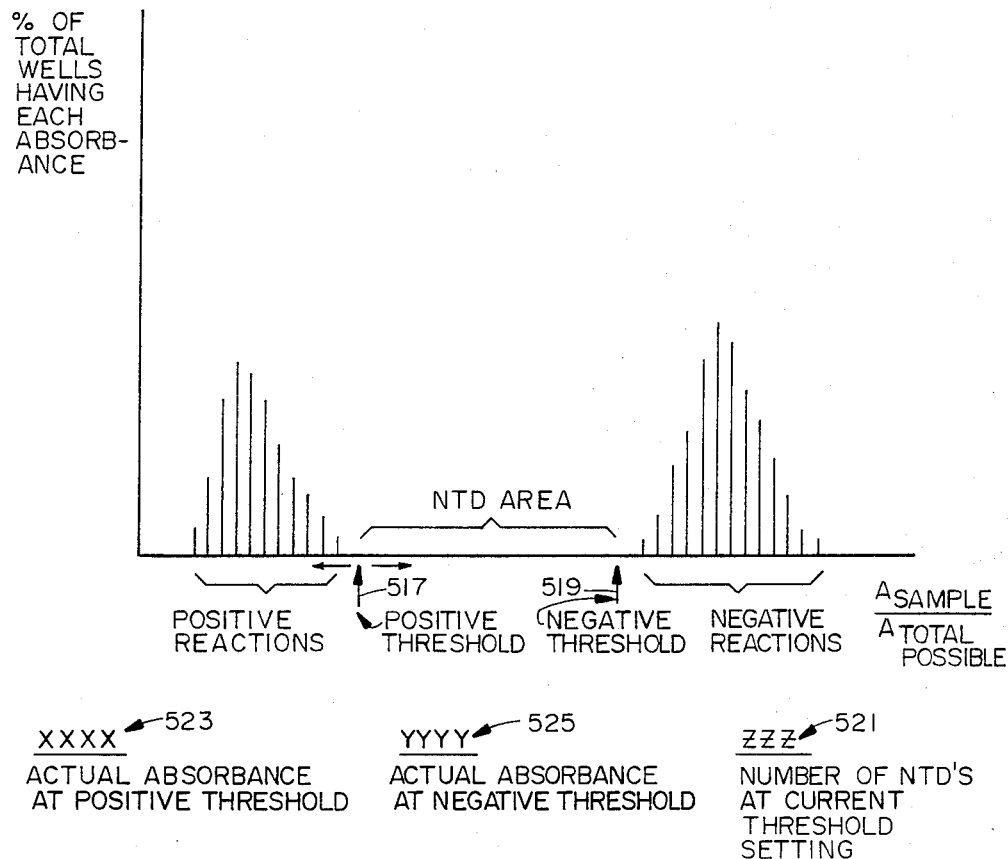
FIG. 12
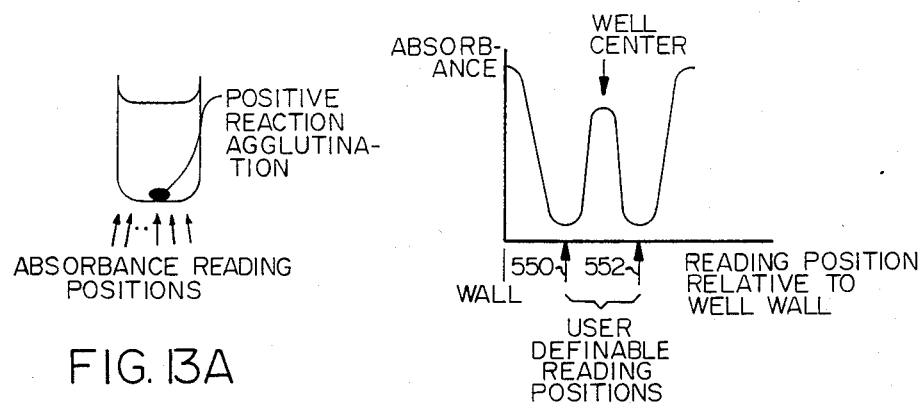
FIG. 13A
FIG. 13B

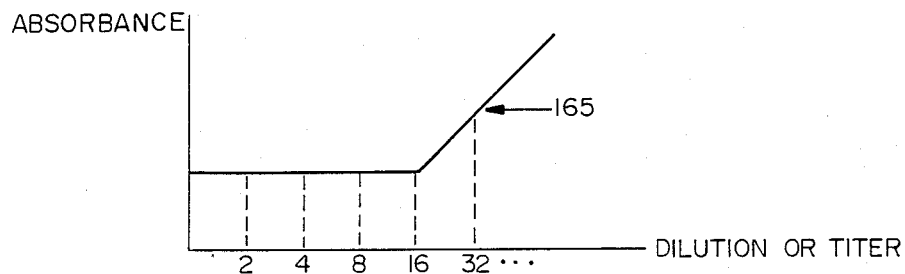
FIG. 14
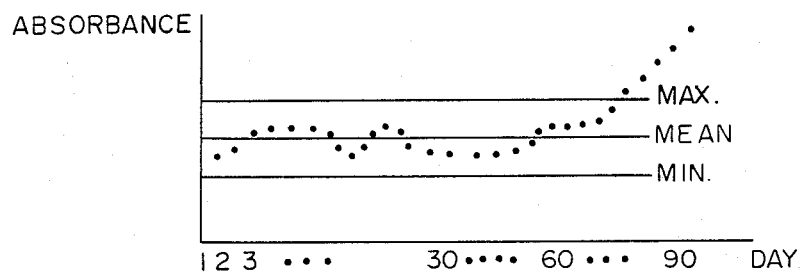
FIG. 15
| WBN | KNOWN WBN TYPE | EXPERIMENTALLY DETERMINED BLOOD TYPE & TEMPLATE |
|---|---|---|
| 123 | A POS | B POS + + – – – + + |
| 135 | B POS | A POS + – – + + + – + |
| 620 | O | O  – – + – – + + |
FIG. 16

USER CONTROLLED OFF-CENTER LIGHT ABSORBANCE READING ADJUSTER IN A LIQUID HANDLING AND REACTION SYSTEM

This application is a continuation-in-part of Ser. No. 788,998, filed Oct. 18, 1985, now abandoned.

CROSS REFERENCE TO MICROFICHE APPENDIX

There is included herewith microfiche appendices, consisting of 10 microfiche and 461 frames, including the hex format object code controlling the various processors in the system.

BACKGROUND OF THE INVENTION

The invention pertains to the field of systems for automatically performing blood typing operations, and, more particularly, to systems for controlling automated liquid handling apparatus to do blood typing and for interpreting the results from a plate reader and for managing the data generated by the liquid handling apparatus and the plate reader apparatus and for printing various reports.

Modern blood banks must perform thousands of blood typing and antibody screening operations and manage the data resulting from such tests. These operations involve the handling of thousands of samples of donor blood, the pipetting of reagents into samples of the plasma and red blood cells from the donor blood and the optical reading of the wells containing the donor samples and the reagents to determining the pattern of positive and negative responses to various reagents. The pattern of positive and negative responses constitutes a template which characterize the blood as being from a particular blood group and having a particular Rh factor. Each test of each donor's blood involves pipetting of multiple samples of that donor's plasmas into multiple wells and pipetting of multiple samples of diluted red blood cell samples into multiple wells. Multiple diluted reagents are then added to the multiple wells containing plasma and red blood samples and various reactions either occur or do not occur depending upon the blood type and the reagent in each well. Typically, these reactions manifest themselves as clumps of protein in the bottom of the well for a positive reaction and no clumps for negative reactions, the pattern of positive and negative reactions determines the blood type.

The blood type can be determined by placing the multiple wells under a strong light source and reading the optical absorbence, i.e., the amount of light which gets through the bottom center of the well. Typically absorbance readings are taken on both sides of the center, bottom of each well, and the results are compared to certain threshold criteria for absorbance. The comparison of the readings will indicate the presence of a clump at the bottom of the well (low absorbance in the off center readings) and therefore a positive reaction or the absence of a clump and therefore a negative reaction (high absorbance on both off center readings).

Clearly, the process of blood typing of thousands of donor samples involves many thousands of liquid handling steps and the generation of many thousands of absorbance readings for the multiple wells devoted to each donor. Further liquid handling steps are involved in automated antibody screening, and some special tests may have to be done by hand on the blood which are not subject to automated liquid handling. Test results from these antibody screen tests and other tests done by hand must be recorded for each donor's blood for which these tests are done. Further, testing procedures for blood typing can change over time in that different dilution values are often needed for different batches of reagents to get the proper absorbance readings. Further, the amount of dilution of the red blood cells should be optimized. The data for the optimal dilution values must be recorded.

Further, other process parameters of the blood typing sequence should be subject to customization to enable the various users to customize their testing procedures to conform to local practice. This data defining the characteristics of each step, such as the amount of each sample to be placed in each well, which wells in which to place samples, the amount of dilution in certain steps, the wells to place reagents in, the number of mixes at various points in the process and various other criteria, should be subject to customization, should be easily changeable, and should be remembered by some mechanism so that it can be automatically invoked each time a procedure is performed without having to look it up every time. Of particular importance is the amount of dilution of each particular reagent which should be used to optimize the absorbance for that reagent and to conserve the amount of reagent used. These reagents are often quite expensive.

Further, it is useful to have a quality control and accountability system such the quality of data generated in the testing is consistently high and the persons performing the testing can be determined. For example, it is useful to know the expiration data for all the reagents in stock and the associated absorbance values for each reagent lot over the period of its usage. It is also useful to compare the test results for known sample types to the results that should have been obtained as a check on the accuracy of the system. It is also useful to be able to generate reports on daily or monthly activities to determine the amount of certain types of blood in stock and where it can be found. The number of "no type determined" test outcomes (hereafter NTD).

Thus, a large amount of data in the form of process controlling parameters and test results are involved in blood typing and antibody screening operations, and a large amount of record keeping for this data is involved. Therefore a need has arisen for a system which can perform these thousands of liquid handling steps reliably and tirelessly and which can handle the thousands of data records which characterize the liquid handling and which constitute the data record for each donor. Further, such a system should be access controlled and implement accountability. It should also ease quality control operations and maintain data useful in quality control efforts. Such a machine should also maintain all test results and be able to communicate them to a mainframe computer for permanent storage or allow them to be archived onto permanent magnetic storage. Such a machine should also enable the automated generation of reports for management.

SUMMARY OF THE INVENTION

The invention is a system for performing a host of functions which aid in the operational work and management of a blood bank. The invention consists of various off the shelf components and a custom designed liquid handler combined in one system, all controlled by a comprehensive software resident in a host computer which allows the user to control blood typing and other liquid handling operations in the liquid handler and to manage the data which results therefrom. The system automates: much of the liquid handling involved in processing donor samples for ABO/Rh blood typing tests and antibody screening; sample and plate identification using a bar code reader; plate reading for the ABO/Rh tests; record keeping for quality control data and test results for individual samples; access to information on test status; and printing of laboratory records and transmission of information to a mainframe computer for on-line storage.

The physical system includes a Digital Equipment Corporation PDP-11 MICRO with a 10 megabyte hard disk and a VT220 terminal. The host system 20 runs a commercially available operating system. The control software is resident in the host. It is coupled to a custom designed liquid handling system which has several microprocessors resident therein which control various stepper motors, bar code read heads and monitor various sensors. The process controlling parameters to control operations of the liquid handler come from the host computer after being defined by the user at the host terminal. Once the process parameters are loaded, the resident software in the liquid handler controls various transfers of donor blood plasma and red blood cells to various wells in plates loaded by an automated plate reader. The resident software also controls dilution of the red blood cells before depositing them in wells and the transfer of specified quantities of various types of reagents into the wells containing the donor's blood plasma and diluted red blood cells. Each plate can hold samples from eight donors, and the donor samples are stored in test tubes in a circular, rotating lazy-susan-like device which is controlled by the software of the liquid handler.

The plates so filled are then unloaded by a plate handler device, and manually transferred to a plate reader Model Autoreader EL309 manufactured by Biotech Instruments which is also coupled to the host. The plate reader then obtains absorbance readings on the wells in the plates after reading the bar codes on each plate. These absorbance readings for each well on each plate are sent to the host with the bar code of the plate for interpretation.

The host knows which wells of each plate contain samples from which donors having obtained this information by downloading the bar code data read by the liquid handler from the donor test tubes and the plates that received samples from each tube. The absorbance values are interpreted by plotting histograms for the number of samples having each absorbance for each different type of reagent. The user is then allowed to define the threshold values between the positive and negative reactions for each reagent by viewing the histogram and graphically moving an arrow to the desired threshold value. A "no man's land" region where the absorbance does not clearly indicate either a positive or a negative value is also defined, and samples having absorbance values falling in this region are tagged as NTD. The user defined thresholds for each type of reagent define "templates" or patterns of positive and negative reactions which will define each particular blood type. The absorbance values for each sample are then compared to these templates and typed as to their blood group type.

The host is also coupled to a printer, and the user can request various pre-formatted management reports. The host is also coupled to an orbital shaker and a centrifuge for re-suspension and re-separation of liquids and sample cells during some system operations.

The host software also contains routines for implementing quality control operations. Such operations include verifying test procedures by processing a small number of known blood type samples and checking the experimental data against the known results, and verifying that the dilution of cell suspension reagents and donor cells produce absorbances in the proper range. The system can also test the titer of antibody reagents.

The data management functions of the invention include the management of data in the form of: test procedure parameters for liquid handling, plate reading and histograms; quality control data consisting of reagent lot numbers and expiration dates with associated absorbances of these reagent lots over the period of their usage; test results including blood groups and probable type; manually added data from such tests as DU tests, antibody screens, hepatitis, HTLV III, CMV, RPR and other tests; and test status for the day of a range of parameters such as the number of A+ samples that have been processed, the number of NTD's during the day and the status of testing for particular plates.

BRIEF DESCRIPTION OF THE DRAWINGS

FIG. 12 is an illustrative histogram for a single reagent illustrating the meaning of adjusting the thresholds used in interpreting test results.

FIG. 13A shows a typical well bottom with a positive reaction button.

FIG. 13B shows a typical graph resulting from a positive reaction button.

DETAILED DESCRIPTION OF THE PREFERRED EMBODIMENT

Figure 1:
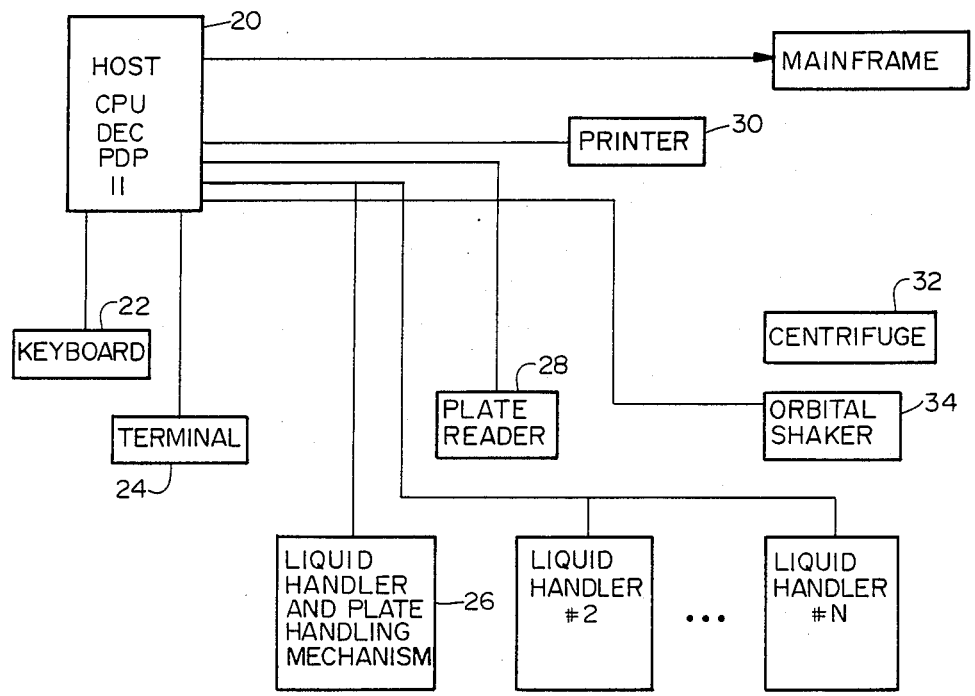
FIG. 1 is a block diagram of the interconnection of the various components of the system.

Referring to FIG. 1 there is shown a block diagram of the system of the invention. The system is comprised of a Digital Equipment Corporation PDP-11 MICRO host computer 20 which coordinates the activities of the system under the control of the resident software included herewith as the appendices and the user (not shown) who enters commands through a keyboard 22 in response to information displayed by the software on a terminal 24. The host computer 20 runs the commercially available Micro RSX operating system for the PDP 11/23, 11/53 or 11/73 computer versions available from Digital Equipment Corporation. The application software which implements the functions described herein is included herewith an appendix. The host computer is coupled by RS232 serial ports and connecting cables to a number of liquid handling and plate handling mechanisms of which liquid handler 26 is an example. The preferred embodiment of the system can control up to 8 liquid handlers. The details of the liquid handlers and plate handling mechanism are given in a copending U.S. pat. application assigned to the assignee hereof entitled "Automated Liquid Handling Apparatus And Process With Plate Handler", filed Oct. 18, 1985, Ser. No. 789,945, now abandoned, and another U.S. pat. application entitled "Liquid Manipulation Device and Method", filed Jul. 5, 1985, Ser. No. 752,449, now abandoned, both of which are hereby incorporated by reference. The object code for the liquid handler disclosed in the above identified patent application has been changed somewhat since the filing date thereof. The latest object code is included herewith in the appendices hereto. The object code appendices are labelled for the particular microprocessor in the liquid handler for which each is intended.

The host 20 is also coupled by an RS232 link to a plate reader 28 which optically reads the absorbance values for samples in various wells in plates filled with samples and reagents loaded from the liquid handler. The plate reader is commercially available from BioTek Instruments, Inc. under the designation Autoreader EL309.

The host 20 is also coupled by an RS232 link to a printer 30 upon which the host 20 prints the various reports of which the system is capable. A centrifuge 32 and an orbital shaker 34 are also part of the system but are not connected to the host 20. The centrifuge and orbital shaker are commercially available off the shelf components and are used to process the plates after the samples and reagents have been put in the wells by the liquid handler 26 and before the plates are loaded in the plate reader 28. Collectively, the above described system may hereafter be referred to as the ProGroup TM automated blood typing system or the system.

The ProGroup TM automated blood typing system automates many aspects of the blood typing and grouping procedures performed in blood banks. This section provides a brief introduction to the functioning of the system.

ProGroup TM Automated Blood Typing System Functions

The major ProGroup TM automated blood typing system functions are broadly defined below. ProGroup TM automated blood typing system automates:

much of the liquid-handling involved in processing donor samples for ABO/Rh tests and antibody screening, sample and plate identification using a bar code reader, plate reading for ABO/Rh tests, record keeping for quality control and test results for individual samples, access to information to test status, and printing of laboratory records and transmission of information to a mainframe computer for on-line storage.

ProGroup Automated Blood Typing System Benefits

The ProGroup TM automated blood typing system is a flexible system, designed to adapt to the way work is already organized in the user's laboratory. The user defines the way he or she wants particular procedures carried out, and ProGroup TM automated blood typing system executes these tasks at command.

Automating liquid-handling makes test results more reliable, and allows employment of lab workers having less skill. Features like computerized data management techniques and the built-in bar code reader reduce the incidence of operator error.

ProGroup TM automated blood typing system does not require any previous experience with automated liquid-handling equipment, or with computers.

ProGroup System Overview

There follows more detail on the individual components of the system.

Liquid-Handler

The liquid-handling portion of the ProGroup TM automated blood typing system consists of the following items.

Figure 2:
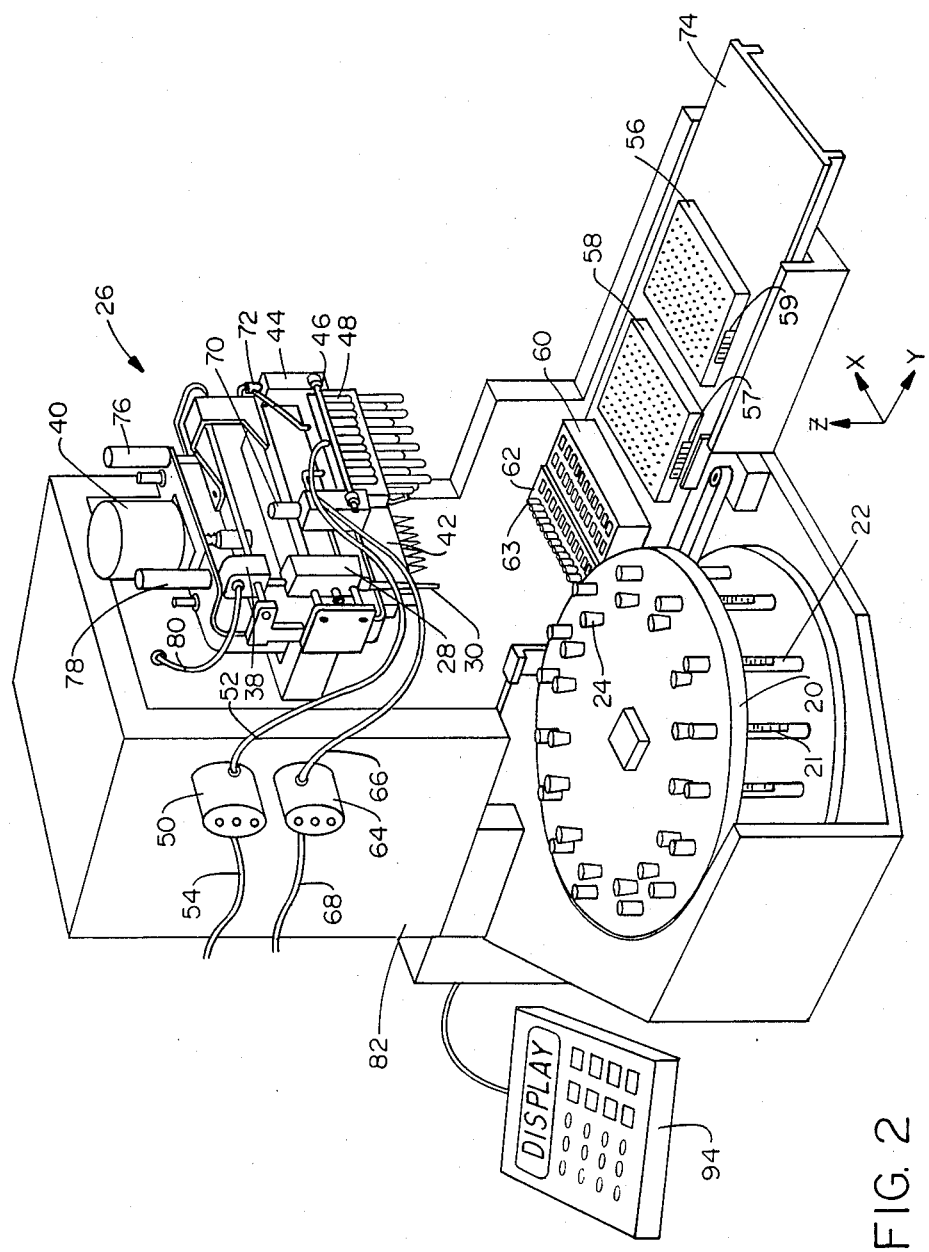
FIG. 2 is perspective view of the liquid handler of the system.

ProGroup TM automated blood typing system liquid handler 26, shown in more detail in FIG. 2, automates the pipetting of donor plasma directly from a carousel 20 of tubes 22 into designated wells of a microplate. The ProGroup TM automated blood typing system mixes donor red blood cells with diluent in designated proportions before transferring the cells to the wells of the microtitre plates 56 and 58. ProGroup TM automated blood typing system fills the ABO/Rh plate 56 and the antibody screening plate 58 with the appropriate reagents from a reagent trough 62. The ProGroup TM automated blood typing system liquid handler includes four permanently mounted liquid delivery heads (X, Y head 28, 12 channel head 42, fill manifold 46, and wash head 44. One or several of these can be used in the course of a single procedure, since there is no requirement to remove one head to install another. The X, Y head and 12 channel head use disposable pipette tips 24 and 63 of several sizes to minimize cross-contamination. The ProGroup TM automated blood typing system accurately transfers volumes between a minimum of 10 ul and a maximum of 200 ul.

Two identical bar code readers (not shown) are built into the liquid-handler: one for reading the bar code 21 on the sample tube (actually located above the top surface of the carousel 20, and the other for reading the bar code 57 and 59 on the microplates (actually located on the other sides of the plates). The bar code on the sample tube is the basis for the Whole Blood Number (WBN) that identifies the donor sample. The bar code on the microplate allows the system to pair the test results from the plate reader with the WBN of the sample donor. The bar code readers can recognize Code Bar or Code 39 labels.

Plate Stacker (not shown) holds six 96-well microplates for ABO/Rh testing. Each plate can accommodate samples from eight donors. These plates are fed into the liquid-handler 26 one by one for processing. Once filled, a plate is automatically transferred off the bed 74 of the liquid-handler, into the other rack of the plate stacker.

Plate Reader

The Plate Reader 28 reads ABO Rh plates automatically and transmits data points to the ProGroup TM automated blood typing system host computer 20 for interpretation. The results are reported by group and type, or as NTD (No Type Determined) readings. An NTD sample can be reread automatically with the plate reader, in which case the results stored on the computer are updated automatically. Alternatively, the row of wells can be examined visually, or the liquid handling and the reading of that sample can be repeated manually. In the latter case, the user inputs information through the computer keyboard to modify the results of the sample processing procedure.

Orbital Shaker

The ProGroup TM automated blood typing system includes an orbital shaker 34 as part of the system. The shaker is used to resuspend the cells after the liquid handling is complete, and then again after the plate has been centrifuged. The orbital shaker can accommodate up to eight plates.

Centrifuge

The centrifuge 32 can be an instrument such as the Beckman TJ-6R Tabletop Centrifuge. It is used in a known manner on the plates from the liquid handler 26 before they are placed in the liquid handler.

Host Computer

The host of the ProGroup TM automated blood typing system is the computer 20, called the host computer 20. The host computer 20 directs the operation of the liquid handler 26 and the plate reader 28, and manages the data generated by the other equipment. The user primarily interacts with the ProGroup TM automated blood typing system through the host computer 20. The user uses the host computer 20 to select the function the user wants the ProGroup TM automated blood typing system to perform, and to view stored data in tabular or graphic form. The host computer 20 allows the user to modify data that has been created through automatic procedures. The user can also enter additional information pertaining to donor samples, such as antibody screen results, or Hepatitis and HTLV III results.

The host computer 20 is a DEC MICRO PDP-11 computer with a 10 Mbyte hard disk and a VT 220 terminal with graphics capability. The computer 20 runs the software included herewith as Appendix A on the RSX11 operating system which is commercially available from Digital Equipment Corporation.

Printer

The ProGroup TM automated blood typing system also includes an LA50 dot matrix printer 30 from Digital Equipment Corporation. The printer is connected to the computer, so the user can quickly generate hard copies of laboratory records.

The ProGroup TM automated blood typing system is used by laboratory personnel at three levels:

The Technician, who operates the machine on a daily basis, running test and printing results.

The Supervisor, who performs quality control procedures, adds to or revises test data as necessary, handles the storage of information on the ProGroup TM automated blood typing system host computer 20, and data transfers data to a mainframe computer.

The Director, who creates the initial framework for the ProGroup. This includes tasks such as defining who will be using the system, how the tests will be carried out, and how test results should be interpreted. The Director modifies this framework as necessary, to reflect changes in system users, test protocol, etc..

Security Precautions

The system utilizes a user privilege table and user identification at logon time to guarantee accountability and to insure that only users with the proper authorization have access to certain portions of the program and certain data files.

The following publicly available documents are incorporated by reference for support material.

MICRO PDP-11 System Owner's Manual Digital Equipment Corporation.

Pro/Pette Liquid Handling System User's Manual Cetus Corporation.

Automated Microplate Reader Model EL309 Operator's Manual, Bio-Tek Instruments, Inc..

Installing and Using the LA50 Printer, Digital Equipment Corporation.

LA50 Programmer's Reference Manual, Digital Equipment Corporation.

Orbital Shaker User Manual.

ABO/Rh Testing

ProGroup TM automated blood typing system automates the typing and grouping of donor samples. This section describes the liquid-handling, resuspension, and plate reading tasks the ProGroup TM automated blood typing system performs for ABO/Rh testing.

Liquid-Handling Functions

The ProGroup TM automated blood typing system liquid handler 26 transfers donor plasma out of the tubes 22 into designated wells of a microplate 56. It also transfers donor red blood cells into a special predilution block 60, mixes the cells with a defined quantity of diluent, then pipettes them into the appropriate wells of the microplate 56. Then the ProGroup TM automated blood typing system fills the plate with the reagents from the reagent plate 62 for the assay.

Options

Figure 3:
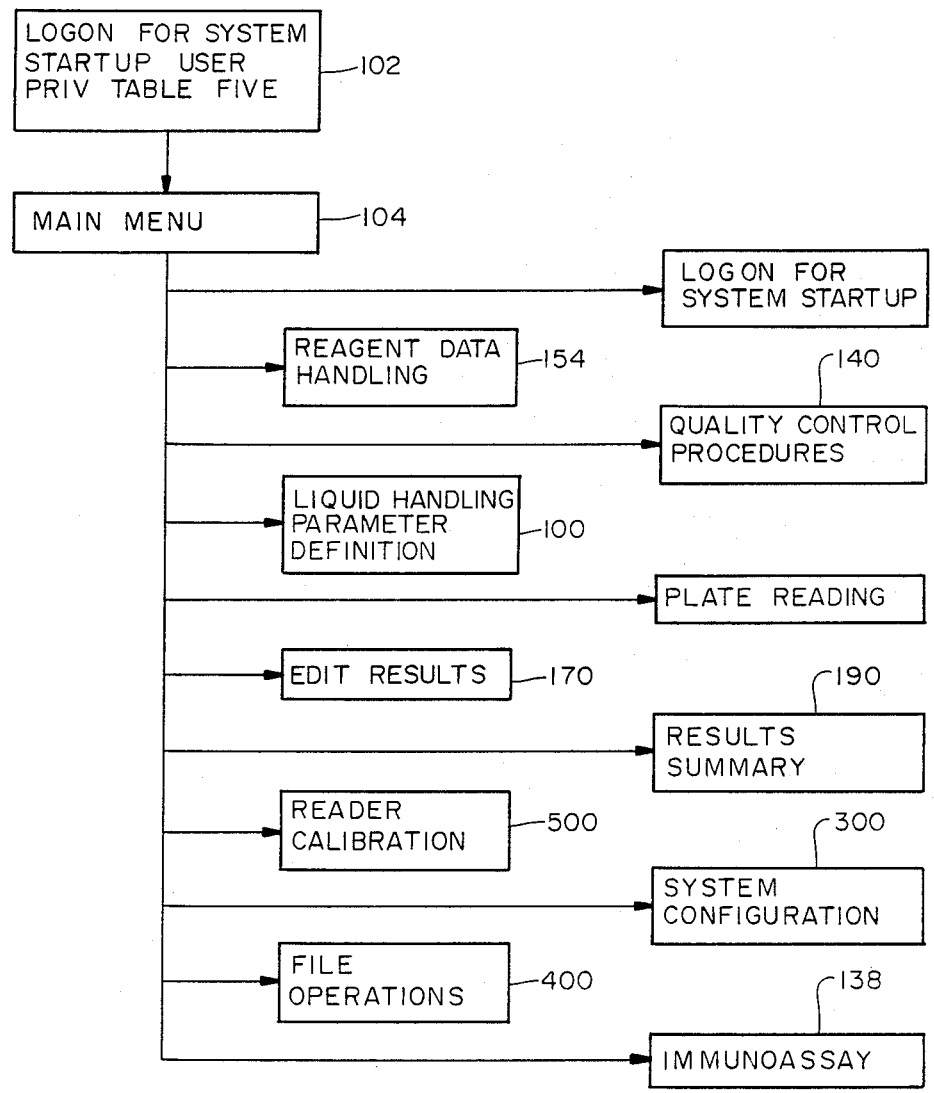
FIG. 3 is a flow diagram of the user options for vectoring processing to various sub-functions that the system can perform.
Figure 4:
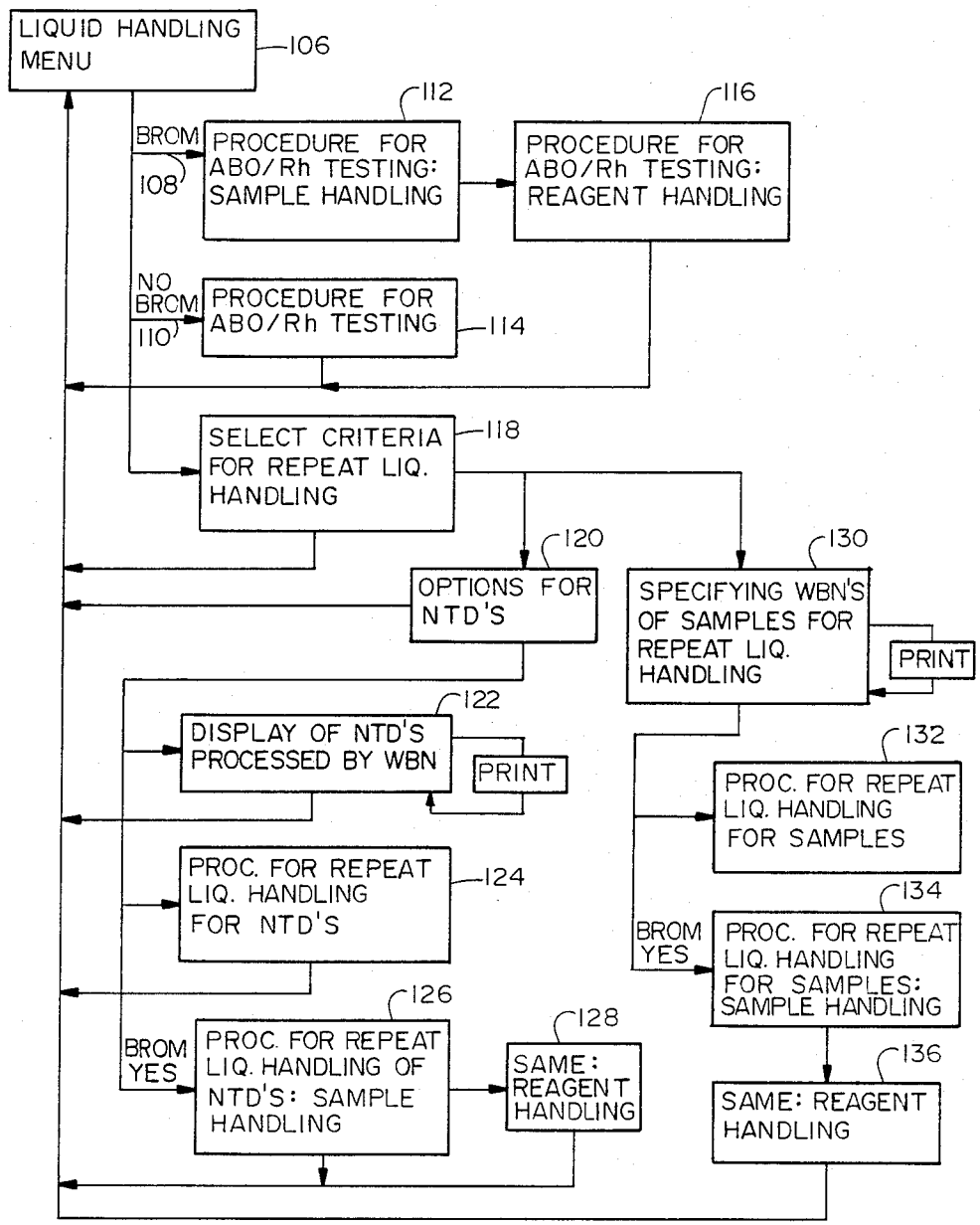
FIG. 4 is a flow diagram for steps performed in allowing the user to customize the process parameters controlling liquid handling operations.

Referring to FIG. 3 there is shown the main menu and logon process. Referring to FIG. 4 there is shown the liquid handling process flow chart for the organization of the software if the liquid handling parameter definition menu selection 100 is selected in FIG. 3. FIG. 4 would be reached after the user identified himself in the logon step 102 and was accepted as a permissible user. Processing would then vector to the main menu screen 104 wherein all the options shown in FIG. 3 would be presented to the user. If he selected option 100, processing would be vectored to the liquid handling menu 106 after going through a logon step (not shown). The liquid handling menu selection allows the user to specify the process parameters of the liquid handling assay for blood typing, NTD determination and repeat liquid handling with or without bromelin pre-treatment. Since these process parameters are critical to accuracy of results, only supervisors or higher are allowed to log into this function of the system. The user specifies the following aspects of liquid-handling for the ABO/Rh test:

whether or not a Bromelin pre-treatment is being used, choice 108 or 110, which blood typing test should be executed (the options are A, B, (A,B), Rh, Cell Suspension, A1, A2, B, and Serm Blank), step 112 and, what test format is being used (i.e., which tests are being carried out in which columns of the microplate to define the format and arrangement of the template, i.e., the pattern of positive and negative reactions which define the blood type), step 112.

The liquid handling may be done on the plates in any order and the plates may be read in any order. The liquid handlers such as device 26 read the bar codes of all the tubes containing donor samples that are pipetted into a particular plate. These bar codes are sent to the host computer 20 along with the bar code of the plate into which samples from the identified tubes were placed. The host computer knows which rows of each plate contain aliquots of blood from each donor because the control software of the liquid handler always places samples in the plates in the same order relative to the order of the tubes from which the samples were removed. The identification data of the plates and the WBNs that are in each plate are stored by the host computer in a lookup table along with any tag data that the liquid handler appends to the identification data for the plate bar code. Such tag data can include data that the plate is a steps off center plate (this will be explained more fully below) or is a donor cell suspension or reagent cell suspension plate etc. Because this data is permanently stored in a look up table, the order in which the plates are read by the plate reader is unimportant. The plates can be loaded in the plate reader in any order. The plate reader then reads the bar code for each plate and sends it to the host computer 20. The host computer then looks up the bar code in the look up table, and determines if any special instructions need to be sent back to the plate reader, e.g. as to wavelength to be used for the light or whether or not to do a steps off center series of light absorbance readings.

Parameters

The user defines the test protocol by specifying in steps 114 and 116 for no bromelin and bromelin pretreatment respectively the:

volume of donor plasma to be pipetted into the wells of the microplate, volume of donor cells, the volume of diluent to be mixed with the cells (thus the concentration of the donor cell suspension) and the number of mixes, concentration of the reagent cell suspension, and titer of the reagent antisera.

Liquid Handler Set-Up

Bar coded tubes containing properly prepared donor blood samples are loaded into the ProGroup TM automated blood typing system carousel. The carousel holds 48 tubes and 48 ProGroup TM automated blood typing system disposable tips. The carousel mounts at the side of the ProGroup TM automated blood typing system liquid-handler. A set of six 96-well microplates is loaded into the plate stacker on the other side of the liquid-handler. Each plate can hold sample from eight donors.

Reagents for the test, including properly diluted cell suspension and antisera are placed in a row of wells in the reagent MicroTrof 62, along with a set of 12 tips. This MicroTrof also contains a row of reagents and a row of tips for the antibody screening test to be described later herein. The reagent MicroTrof is placed at the back of the liquid-handler bed 74.

The predilution block 60 is placed just in front of the reagent Microtrof. The block contains a trough of diluent, and several wells where the donor cells are mixed with diluent.

ABO/Rh Testing Procedure

When the liquid-handler is set up and ready for operation the first step is to carry out the automatic homing and priming procedure. Then the user pushes the START key on the hand-held controller 94. The plate stacker places a 96-well plate on the liquid-handler table, and the bar code 59 on that plate is read. The bar codes 21 on the first group of eight tubes are also read.

Then the liquid-handler picks up the first ProGroup TM automated blood typing system tip from the carousel and withdraws the appropriate amount of donor plasma from the top of the tube. Aliquots of plasma are placed, one by one into the wells of the plate 56 that are designated for reverse typing tests. Next the liquid-handler withdraws the required quantity of donor red blood cells for the forward typing tests. Aliquots of cells are placed into the wells of the predilution block 60, which already contain the required amount of diluent. This diluent had been placed in the wells by the microprocessor of the liquid handler previously in accordance with data received from the host regarding how much dilution the supervisor wants in the test procedure for red blood cells. The diluent and cells are mixed according to data regarding how many mixes that are desired which was specified by the user and sent from the host to the liquid handler, and then the mixture is pipetted into the forward testing wells of the microplate. The used ProGroup TM automated blood typing system tip is then ejected into a used tip container (not shown).

When the microplate 56 is filled with donor samples, the 12-channel head picks up reagents from the reagent Micro-trof 62 and fills the row of the plate 56 containing the first donor's samples with the pattern of reagents specified by the user in the liquid handling procedure set-up step previously described (the user must fill the reagent trof 62 wells with the proper reagents in accordance with the desired pattern). The row of Pro/Pette tips used for this operation is then ejected back into the Microtrof.

At this point, the liquid-handling on the plate is finished. The plate is loaded back into the plate stacker to await completion of the remaining five plates in that group.

When all six are done, they are moved to the orbital shaker for resuspension. Next they are centrifuged at low speed to cause the cells to settle. Then, they are resuspended. This sequence of steps disperses the cells when the test results are negative, but causes the cells in a positive test to clump together in a tight button at the bottom of the well.

The final step is to load each plate into the automatic plate reader. Plate reading can occur no less than three minutes, but no more than ten minutes after the final resuspension of the cells. The plate reader reads one row of 12 wells at a time, making two-off-center readings on each well as is known in the art. The reading with the higher absorbance is discarded and the lower reading is transmitted to the ProGroup TM automated blood typing system host computer 20 20 for interpretation. The computer compares the reading for each well with defined threshold values (set by the user as described below) to determine whether the data point represents a positive or negative result for that test.

It requires about a minute to read each plate, then the plate is removed and placed in a rack for storage. The plate can be retrieved if it is necessary to reread a row.

The tubes from the carousel are also placed in a rack. If the results indicate that a given samples might be Rh negative, that tube is loaded into a carousel for DU testing.

If the results for blood typing are internally contradictory or indeterminate, the liquid-handling and plate reading must be repeated, either automatically or manually. The user selects criteria in step 118, FIG. 4 for comparison by the host 20 against test results to determine if repeat handling is necessary. For NTD's the user can specify the exact procedure to be followed by the liquid handler upon retesting of these donor samples in steps 120, 122, 124, 126 and 128. For other than NTD's for which the user desires retesting, he can specify the exact procedure to be followed by the liquid handler for this retesting in steps 130, 132, 134 and 136. Tubes that require repeat processing are loaded into another carousel for further scrutiny.

Antibody Screening

The main menu on FIG. 3 has an option 138 for conducting immunoassays for the presence of some antibodies such as HTLV and others. Because these assays differ widely, the software allows the user to link files to perform the assay in pieces. By asking the user which assay he wishes to perform, and the starting file the user can have flexibility in the types of assays he performs. The user can start with the first file, customize its parameters and put a linking address in the linking field of the first file to the next file he wishes to perform. After all the files are properly customized, the liquid handler will, upon command, perform the first file in the sequence and then proceed to the linked file and perform it. Many different types of assays can be performed in this manner.

After the entire antibody screening plate has been filled with sample, the 12 channel head picks up a row of short tips from the front row of tips in the reagent MicroTrof TM. These tips are used to aspirate sample from the front row of wells in the reagent wells in the reagent MicroTrof 62 which contain reagents necessary for the performance of the antibody screening test. The entire plate 58 containing donor plasma samples is filled with the reagents, and the user removes the antibody screening plate manually for interpretation of the results manually. The ProGroup TM automated blood typing system only delivers donor samples and reagents to the plate for antibody screens and performs no further operations.

Options

The user can specify that the antibody screening test be carried out with one reagent, with two reagents, or with three, as test protocol directs.

Parameters

The user defines the volumes of sample plasma and reagent to be pipetted into the microplate.

Quality Control

Quality Control Procedures

The ProGroup TM automated blood typing system enhances quality control of test procedures. Specific ProGroup TM automated blood typing system functions are:

verify test procedures by processing a small number of known samples and checking the experimental data against the known results.

verify that the dilution of cell suspension reagents and donor cells produce absorbances in the proper range, and check the titer of antibody reagents to insure that the proper dilution levels are being used for good readings without excessive reagent consumption.

Testing Known Samples

One of the ProGroup TM automated blood typing system's quality control functions enables you to assay known samples. The user can thus ensure that the system is functioning correctly in terms of test format: that reagents are being placed in the proper rows of the microplate and that donor plasma and cells are being pipetted into the appropriate destination wells. This QC procedure also indicates whether the liquid-handler and plate reader are working properly, and validates the stored thresholds used to interpret test results. Further, the reagents received from reagent manufacturers such as A1, A2 and B cells vary widely from lot to lot in their dilution strength. Manufacturers dilute these reagents for sale, but the dilution is not always consistent from lot to lot. Further, the cells have a shelf life and lose their potency as time goes by. To get accurate results, the strength and dilution of the reagents must be checked from time to time to insure that the absorbance values obtained from use of the reagents is normalized to some common denominator or reference point.

Another aspect of the quality control procedures the system is capable of performing is the facility to allow the user to compare known blood type samples to the results obtained by the system. That is, the user may have the system perform automated liquid handling and automated blood typing of a group of known samples and then may graphically compare the experimentally determined templates to the known templates for the known blood types processed. The quality control test by assaying known samples is done by selecting option 140 in FIG. 3 which vectors processing to the process flow shown on FIG. 5A starting at block 142. Block 142 represents the step of having the quality control operator log his identification code into the system. The test is done by placing test tubes of known blood types in the carousel and assigning them WBN's on the host computer and indicating the particular blood group and type for each WBN. This process of entering the WBN's of the known blood type samples is symbolized by step 144. Steps 146, 148 and 150 represent information screens telling the user how to set up the liquid handler so that the liquid handler has the known samples in the carousel and has the proper liquid handling file called up via the handheld controller for execution by the liquid handler. The liquid handler then performs the ABO/rh type liquid handling procedures described in the U.S. pat. applications describing the liquid handler which are incorporated by reference. The specific file for this quality control procedure includes instructions to tag the bar code data from the plates being processed for this procedure with a data tag that is stored with the bar code in a look up table. The plates with the reagents and donor samples are then removed by the operator and put on the plate reader and the absorbance readings of the various wells containing the various reagents are taken. These steps are symbolized by the block 153 in FIG. 5A. The plate reader also reads the bar codes from the plates it reads and sends them to the host computer 20. The host looks up the bar code data and finds that the absorbance data is intended for a quality control chart. The data is then stored in a file that stores this type of quality control data, and it is processed for graphical display. FIG. 16 is an example of the type of quality control graphic display which will be displayed by the host computer. Block 153 represents the process of storing the absorbance data received from the plate reader and processing it into the graphical display shown in FIG. 16. Block 152 represents the process of actually displaying the data in the graphical format shown in FIG. 16. As seen in FIG. 16, the known blood type and group for the WBN's tested as entered by the user is displayed in one column. Another column displays the experimentally determined blood types and the experimentally determined blood typing templates, i.e., the pattern of positive and negative reactions to the various reagents used in the forward and reverse typing process. The user can compare these experimentally determined templates to the known template for each blood group and type.

Checking Dilution Ratios

The ProGroup TM automated blood typing system carries out ABO/Rh tests using reagents at a fraction of their standard concentrations. Positive and negative test results on the ProGroup TM automated blood typing system are distinguished more or less sharply, depending on the concentration of the reagent and donor cell suspensions. This differentiation results because a substantial excess of antigens or antibodies causes the red blood cells to return into suspension. In general, the optimal dilution for these assays is around 1:3. FIG. 14 shows a graph of the typical absorbance for various levels of dilution of an antibody reagent with a sample which is known to cause a positive reaction with that antibody reagent. Antibody reagents are very expensive, and their concentrations from the manufacturer vary considerably. These reagents are reacted with donor cells in forward typing to determine the type of blood the patient has in a process which is well understood by those skilled in the art. Thus, at times it is necessary to dilute the antibody reagents to get uniform results and to not waste money. The absorbance graph of FIG. 14 is derived by taking a serial dilution of an antibody reagent and mixing the reagent with 3% bovine serum albumin and reacting it with samples from known AB/positive donors. A positive reaction will occur at some dilutions and not at others. The plates are then all read, and the absorbance data is plotted. The absorbance of the off center readings of the plates will be small for dilutions having sufficient concentrations to react positively. However, for dilutions of insufficient concentration to cause the reaction, the absorbance values for the off center reading will rise as shown at 165. The user will know that the optimal dilution to achieve good positive reactions is a dilution slightly more concentrated than the dilution at which the absorbance value starts to rise. In the graph of FIG. 14, the optimal dilution is 8 since that the most cost effective reagent dilution where a good positive reaction is achieved. This number is hypothetical and for illustration purposes only.

FIG. 15 shows a graph of the type of quality control graph which the system plots to check the quality of the reagent and donor cell suspensions. The graph shows absorbance of the reagent cell resuspension for a negative backtyping reaction between the reagent cells of interest and bovine serum albumin (3% BSA) on the vertical axis and the day or time of the test on the horizontal axis. Each point represents the absorbance of the suspension of reagents in a well where the reagent has been diluted to the proper dilution ratio in accordance with the above noted procedure and has been shaken to put the cells in suspension after centrifugation to collect all the cells at the bottom of the well. The purpose of this procedure is to check the quality of the processing by the liquid handler 26 of the dilution and the quality of the resuspension process in the orbital shaker 34 after centrifugation. The shaking process can be done improperly so that the reagent cells are not properly dispersed throughout the solution. Also the dilution may have been done improperly. Both of these errors will show up as a change of the absorbance of light passed through the solution. The points on the graph of FIG. 15 represent the absorbance values which result on each day when a new dilution of donor cells is made and the resuspension process is completed of the bovine serum and reagent cells for the QC test done each day in preparation for that day's processing. The maximum and minimum values shown in FIG. 15 are constants which are established as the limits of the absorbance range considered acceptable for a reagent cell suspension. As can be seen from the drift out of bounds toward the 60 day mark there is some problem which is developing either in the dilution or in the resuspension procedure which is causing the reagent cell suspension test results shown in FIG. 15 to become unacceptable thereby signalling the user that a problem is occurring. This allows the user to monitor the quality of his reagent cell suspensions to determine that they have been properly diluted into the proper absorbance range and that the resuspension process is being done properly to maintain the quality of test results on donor blood samples using the reagent cell suspensions tested.

The donor cell suspension quality control process is similar and the system makes a similar graph to that shown in FIG. 15. The donor cell suspension quality control checking procedure is important because the positive-negative decision process involves a ratio of the forward typing test absorbances to the donor cell suspension. In order for these ratios to be valid, the donor cell suspension needs to be within the range of sensitivity and linearity of the plate reader. It is important that there be enough cells to give a large enough absorbance to give a reliable separation between the ratios of a positive and a negative reaction. The absorbance of the donor cell suspension is a function of the volume of cells withdrawn from the sample tube, the volume of diluent in the predilution block, the efficiency of the mixing during the cell dilution, the force at which the donor sample tubes and the ABO/Rh plates are centrifuged, and the efficiency of resuspension. Thus, the donor cell suspension is a sensitive indicator of the quality of all these steps or how closely to being correctly done these steps are being performed. The system keeps donor cell suspension records and quality control graphs which are identical to those of the reagent cell suspensions. The system will continue to accumulate data on the daily donor cell suspension procedure preceding the day's testing until a reset option is exercised. The system, as in the case of the reagent cell suspension, will give several information screens which give a synopsis of the procedure to be followed to perform the necessary liquid handling and plate reading to check the donor cell suspensions. In this procedure, the antibody reagents in the ABO/Rh block of the liquid handler are replaced with bovine serum albumin (3% BSA). This insures that there will be no hemagglutination and that resuspension will be similar to that of a negative reaction.

Figure 5A:
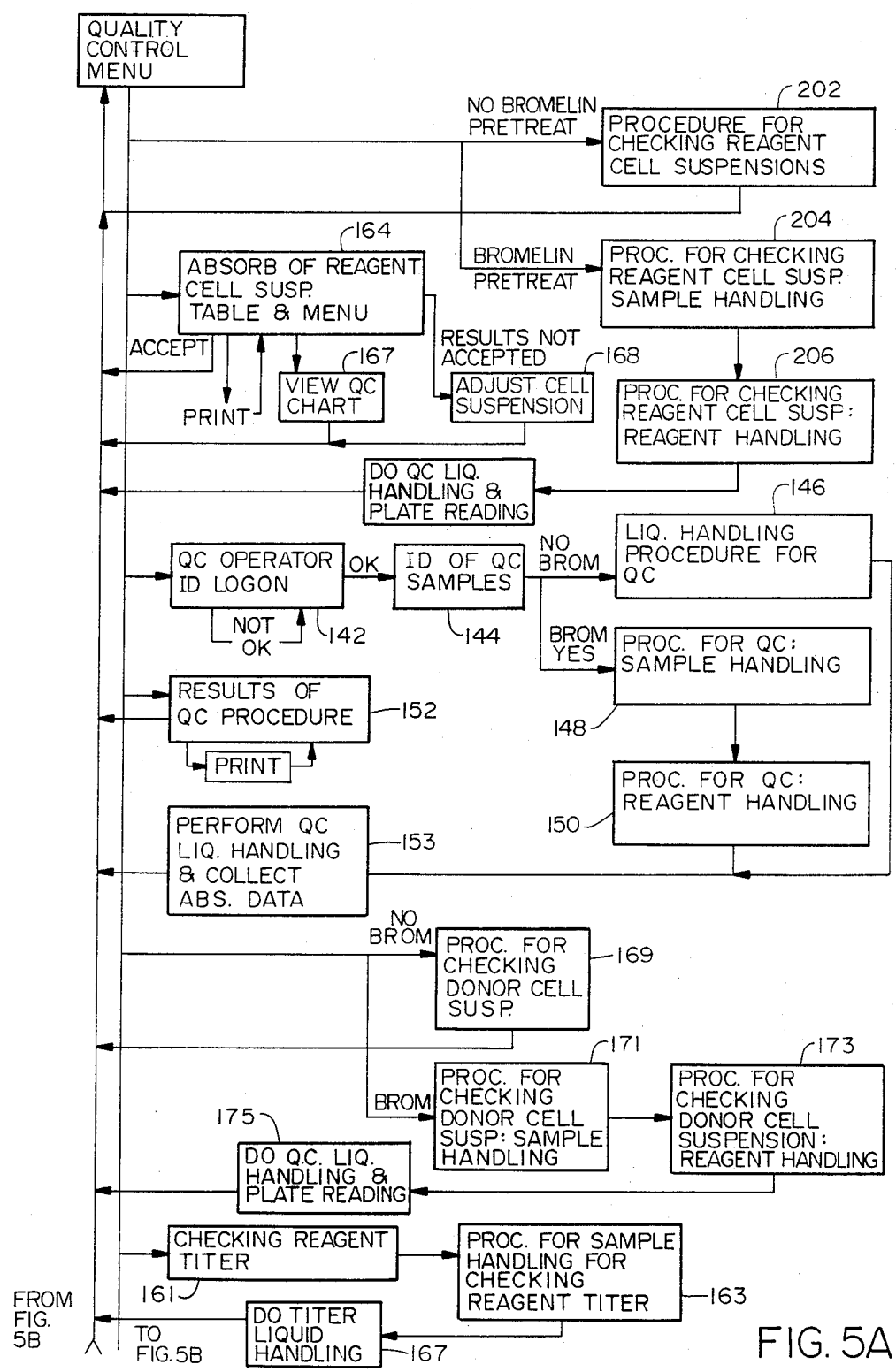
FIGS. 5A and 5B are a flow diagram of the process of allowing the user to monitor and control various quality control functions.

The user uses a special ProGroup TM automated blood typing system function to determine the optimal dilution ratio for a specific lot of antibody reagents used in forward typing by selecting option 154 on FIG. 3. This selection vectors processing to the process shown in FIG. 6. There the user can select option 156 to enter data on the reagents in inventory, their lot number and expiration date, the date the reagent data was entered into the system and the proper dilution for that particular lot of reagent (reagents come in varying concentrations from their manufacturer.) The proper dilution value is determined experimentally by using the process shown in FIG. 5A. The user must select the menu option "check reagent titer" shown as block 161 in FIG. 5A. The system then checks the antisera titer by displaying an informational screen 163 telling the user what to do to perform this process. One of the things the user must do is to make sure the file numbers 14, 15 and 16 displayed on the handheld controller of the liquid handler 26. This alerts the host 20 to tag the barcode of the plate that will contain the serial dilutions of the antisera that the plate is a titer plate and that data from this plate is to be collected from the plate reader and stored in the titer file to process and display a graph like FIG. 14. The user will then set up the liquid handler in the manner described in the information screen of block 163, and the liquid handler will be downloaded with instructions from the host to do a serial dilution and pipetting of the known donor samples placed by the user in test tubes in the carousel into the diluted reagents in the 12 well serial dilution plate. The system will then do a serial dilution on each reagent to be analyzed using the liquid handling portion of the program and will mix aliquots of the known blood type donor cells supplied by the user with the various dilutions of the reagent so as to generate known positive test results in some of the wells of sufficient concentration as symbolized by block 167 in FIG. 5A. The plates are then read, and the system looks up the bar codes in the look up table coming in from the plate reader and determines that the absorbance data coming in from that plate is to be stored in a file and processed for display as a titer graph such as that shown in FIG. 14. The host knows which dilutions were in each well because the host instructed the liquid handler to do a serial dilution in a conventional fashion. Accordingly, the data is sorted and processed according to its well position and the known dilution value for that well. The data may then be viewed graphically in the form of a graph like that of FIG. 14 by selecting the menu option "view titer graphs" symbolized by block 162 in FIG. 5B. The absorbance values will be low for all dilutions until the concentration is too diluted to cause a positive reaction to occur. At the concentration where no positive reaction occurs and at more dilute concentrations, the absorbance will be higher indicating a false negative reaction such as is shown at 165 in FIG. 14. The cursor keys are then used to move the arrow two titers down, and that concentration is selected as the optimum concentration for that reagent lot. Then the system automatically stores the user selected ratio into the reagent data table for that reagent and automatically instructs the liquid handler to dilute that reagent to the user selected dilution every time it is used until the reagent titer is again changed by the user. This ratio must be used consistently throughout that reagent lot to obtain reliable test results.

The control software for the host follows a similar process for donor cell suspensions. The procedures for doing the donor cell suspension are specified in information screens symbolized by blocks 169, 171 and 173 on FIG. 5A for bromelin pretreatment and no bromelin pretreatment. Step 175 represents the process of downloading of liquid handling instructions for the database of the specific file the user has been instructed to select on the liquid handler handheld controller to do the liquid handling for the donor cell suspension. Step 175 also represents the liquid handling by the liquid handler 26 and the process of receiving data from the plate reader when the plates having the donor cell suspensions are read. Block 175 also represents the process of storing the received data in the donor cell suspension file, and processing the data for display as a graph like that of FIG. 15.

Figure 5B:
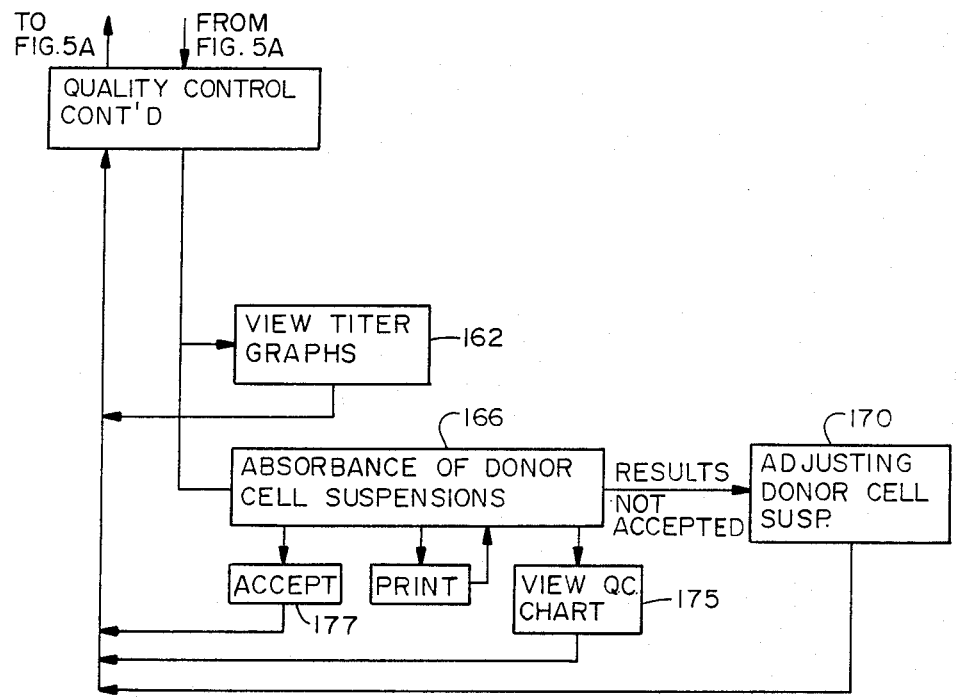
Figure 6:
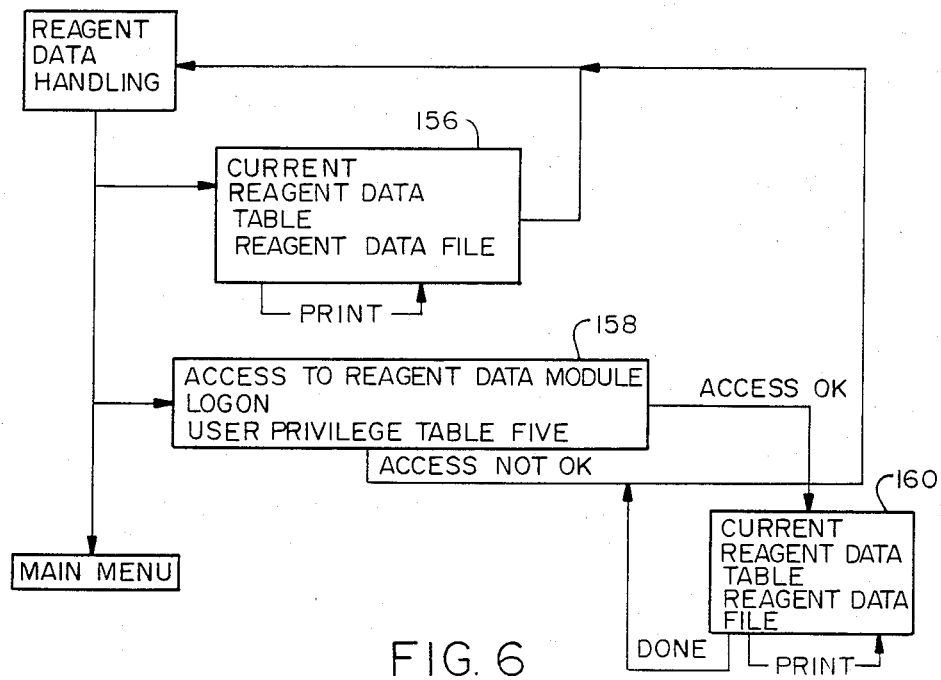
FIG. 6 is flow diagram for the process of allowing the user to create and access various reagent data for use in insuring proper processing and improving reliability of test results.

Block 166 on FIG. 5B represents the process of displaying the results of the donor cell suspension quality control procedures numerically on the terminal of the host. If the user wishes to review the donor cell suspension data graphically in the format of FIG. 15, the host performs step 175 to display the results graphically on the terminal. Block 170 represents the process of instructing the user as to changes that can be made to bring the absorbance of the donor cell suspensions back into tolerance. This information screen is reached if, in response to a prompt from the host, the user indicates the results of the donor cell suspension are not acceptable. If the results are accepted, block 177 is performed where the donor cell suspension data for that day is permanently recorded as part of the donor cell suspension absorbance data file as a permanent record.

The user can modify the reagent data table by selecting option 158 if the user has a supervisor status or higher. If access is granted after the logon, the step 160 can be performed to enter changes in the reagent table.

ProGroup TM automated blood typing system QC procedures allow you to verify that the dilution of donor and reagent cells are the same, and that the absorbances of both fall into the appropriate range (1.2 to 1.6 A.U.). A comparable function tests the dilution of the reagents used for the antibody screen testing.

Data Management

Kinds of Information

The third major function the ProGroup TM automated blood typing system performs is managing the data generated in the course of blood testing procedures.

The host computer has software that enables it to manage four main types of information:

the data governing test procedures, such as the parameters for liquid-handling and plate reading, the histograms that serve as process of instructing the user as to changes that can be made to bring the absorbance of the donor cell suspensions back into tolerance. This information screen is reached if, in response to a prompt from the host, the user indicates the results of the donor cell suspension are not acceptable. If the results are accepted, block 177 is performed where the donor cell suspension data for that day is permanently recorded as part of the donor cell suspension absorbance data file as a permanent record.

The user can modify the reagent data table by selecting option 158 if the user has a supervisor status or higher. If access is granted after the logon, the step 160 can be performed to enter changes in the reagent table.

ProGroup TM automated blood typing system QC procedures allow you to verify that the dilution of donor and reagent cells are the same, and that the absorbances of both fall into the appropriate range (1.2 to 1.6 A.U.). A comparable function tests the dilution of the reagents used for the antibody screen testing.

Data Management

Kinds of Information

The third major function the ProGroup TM automated blood typing system performs is managing the data generated in the course of blood testing procedures.

The host computer has software that enables it to manage four main types of information:

the data governing test procedures, such as the parameters for liquid-handling and plate reading, the histograms that serve as references for interpretation of test results, etc., quality control data, which consists of lot numbers and expiration dates for all reagents, with associated values for the absorbances of these reagent lots over the period of their usage, test results, including blood group and probable type, which are generated automatically. The results for the DU test, antibody screen, and other miscellaneous (Hepatitis, HTLV, III, CMV, RPR, etc . . . ) can be added manually to the information that is already stored for that donor sample.

test status for the day in terms of a range of parameters, such as the number of A+ samples that have been processed already, the number of NTDs that have occurred in the course of the day's testing, the status of testing for particular plates, etc.

The section that follows describes each of these four major categories of data. Then how data is stored in the system, and how the ProGroup TM automated blood typing system safeguards the validity of this information will be described.

Test Parameters

The ProGroup TM automated blood typing system is a programmable system. This means that the user only need to specify once how the user wants the ABO/Rh test to be carried out, and how the user wants the liquid-handling performed for the antibody screen. Thereafter, the user just sets the system up properly, and the ProGroup TM automated blood typing system automatically executes the function just as the user's directed.

The ProGroup TM automated blood typing system also simplifies the work by making certain calculations from the data the user has supplied. For example, on the basis of the test format and sample volumes, the user defines prescribed the ProGroup TM automated blood typing system computes how much donor plasma to pick up and which wells of the ABO/Rh plate to pipette it into.

Because the ProGroup TM automated blood typing system is programmable it may be fine-tune the system to optimize its accuracy. For example, certain test parameters must be adjusted over time. Each new lot of reagents usually requires a slightly different dilution ratio, so the user will need to change the volume of diluent in relation to the volume of donor cells. The user makes these changes by entering the new values just once using option 100 in FIG. 3. The old values in the program are replaced automatically with the new values by the host computer.

Quality Control Data

ProGroup TM automated blood typing system tracks quality control data to help the user verify that the system is performing properly and recognize when parameters need to change.

ProGroup TM automated blood typing system stores the lot number, expiration dates and dilution ratios for all reagents used in the system. The user can use a printout of this information as a convenient way to double-check the reagent values at the start of the workday.

ProGroup TM automated blood typing system also allows the user to compare the mean, minimum and maximum absorbance values for each type of reagent cell suspension and donor cell suspension against the previously stored values. The absorbance of the reagent cell suspensions can be viewed using step 164 of FIG. 5A. The absorbances of donor cell suspensions can be observed using step 166 in FIG. 5B. The object of checking donor cell suspensions is to insure that from day to day, the same number of red blood cells from the donors is placed in the wells to be reacted with the reagents. If different numbers of red blood cells were placed in a well and reacted with the same reagent and both samples were the same type, one test might have a different result than the other merely because of the different donor cell concentration. This would lead to erroneous test results, and should be avoided. The same adverse result can occur if the concentration of reagent cell suspensions varies from day to day. The reagent cell suspension absorbances can be tested and graphed using the step 164 of FIG. 5A. Adjustments in either cell suspension amount can be made using the steps 168 and 170. If the graph of the resulting data points shows a shift, it indicates a deterioration in reagent quality or in the donor cell suspension concentration.

Test Results

The ProGroup TM automated blood typing system also stores information on each donor sample in a data file. The data file is the functional equivalent of a card file, except that the information is stored magnetically on the ProGroup TM automated blood typing system hard disk instead of on paper. The data file for each sample is identified by a Whole Blood Number (WBN) which is derived from the bar code on the sample tube. The carousel number and the position (1–48) pinpoint the location of the tube. The bar code on the plate and the number of the row specify the location of the test wells for that sample. This information makes it easy to locate the wells and the tube should the user need to.

Categories of Test Results

The results of the ABO/Rh tests are entered automatically in the appropriate data file. These results can fall into two broad categories: Resolved, and NTD.

Resolved Results

If the blood group is positively identified, the sample is considered to be resolved.

When the Rh factor is positive, the ABO/Rh testing for that sample is complete. If the Rh factor is negative, the sample is added to a DU list which is a list of WBN's where the presence of the D antigen on the red blood cells is unknown indicating a possible Rh negative blood type. If the results for the Rh factor fall into a no-man's land between the clearcut positive and negative results, the sample is treated as if it were Rh negative. The WBN of this sample is added to the DU list so that further testing can determine the status of the Rh factor.

NTD Results

If the blood group cannot be identified the sample is categorized as an NTD. The ProGroup TM automated blood typing system assigns a NTD if the pattern of positive and negative reagent reaction results for a row of wells does not match any of the stored templates for known blood types. Most commonly, an NTD reflects contradictory results among the various tests.

A sample is also designated as an NTD if a test result falls into no man's land between the Thresholds for the positive and the negative results. An NTD can also occur because the cell suspension or the plasma blank for that row of samples was out of the acceptable range.

Resolving The Sample

The processing of a sample is not complete until the blood group and type have been established.

Figure 7:
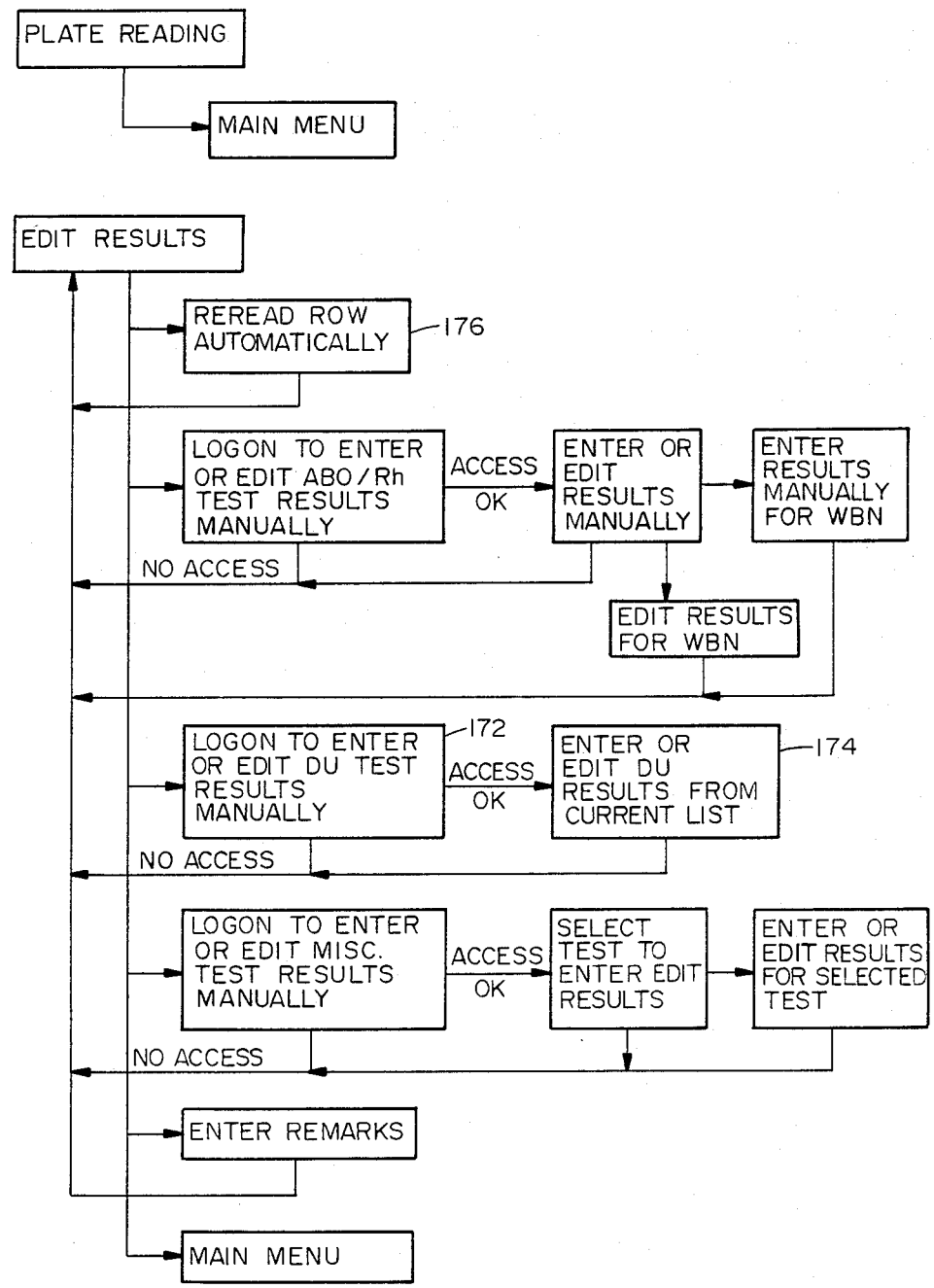
FIG. 7 is a flow diagram of the plate reading function of the system and a flow diagram of the process followed in allowing the user to edit or enter various results from testing.

If a WBN is added to the DU list as a potential Rh negative, the results of the DU test must be entered manually in the data file to complete the sample profile. This is done by selecting option 170 on FIG. 3 which vectors processing to FIG. 7 and selecting option 172 there. If the user logon ID indicates the user is authorized to enter DU results, then access to step 174 will be granted, and the user will be allowed to enter the test results.

If the automatic test procedure produces an NTD, the row can be reread automatically. This can be specified by selection of option 176 in FIG. 7. Or, the entire liquid-handling and plate reading procedure can be repeated automatically. In either case, the new results automatically replace the previous results. Alternatively, the user can inspect the row of wells visually, to see if an apparent positive result was actually caused by a fibrin clot, for example. Or the user can perform the liquid-handling by hand and read the plate by eye. Either way the user enters the test results into the data file by typing the information into the host computer using the process of FIG. 7.

Additional Test Results

The system host computer automatically interprets and stores data for each WBN the ProGroup TM automated blood typing system processes. This data structure accommodates other information as well as the results of the ABO/Rh test procedure. The user can enter results for the following tests:
 antibody screen
 Hepatitis
 HTLV III
 Cytomegalin Virus (CMV)
 Rapid Plasma Reading (RMR)

The invention thus allows the user to organize all the information about a donor sample into a single concise structure.

Testing Status

The system gives the user immediate access to information on test status. The user can ask for:
 the WBN of the first NTD,
 the current DU list,
 the tables of ABO/Rh results for the day
 the status of a particular plate, etc.

The system answers these and many other questions with up-to-the minute accuracy. If the user needs to know whether there's any of a particular blood group being tested, the user can search by group and type to find the WBNs of samples that fit this profile, then determine how far the testing on these samples has progressed.

Working With ProGroup Automated Blood Typing System Data

Figure 8:
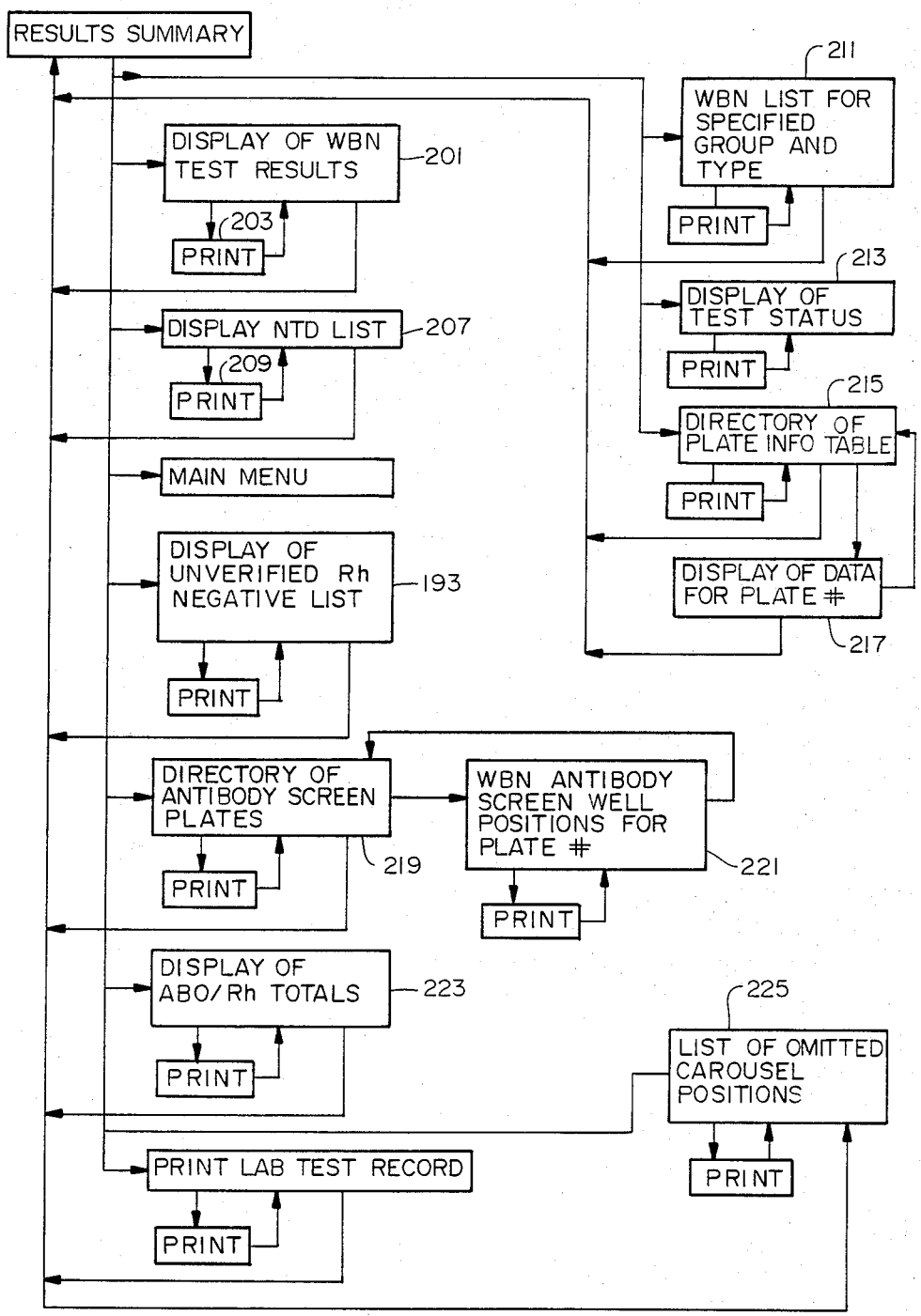
FIG. 8 is a flow diagram for the process followed in allowing the user to specify results summaries the user would like to see.

The information the user inputs and the data the system generates are displayed on the host computer 20 in lists or in graphical format. For example, the WBNs that require DU testing are displayed as a list by selecting option 190 on FIG. 3 which vectors processing to FIG. 8 where step 192 is performed. The results of quality control tests for reagent cell suspension are graphed as a series of values for daily absorbance over the interval of that reagent lot.

The user enters new information or modifies existing data through the host computer keyboard by selecting option 170 in FIG. 3. This is an interactive process. If the user makes a mistake, it's usually easy to correct. And keyboard input is immediately stored on the fixed disk. The user doesn't have to remember to tell the system to "save" data because it happen automatically.

Differentiating Between QC and Data

The system can automatically distinguish between tests that the user runs on actual samples, and the procedures which are used to develop or modify quality control data. The same kind of liquid-handling is involved, whether the user is testing a new donor sample or checking the reagent cell suspension. But the plate reading techniques and data management techniques are different. The system is programmed to recognize which type of work the user is doing, on the basis of which screen is displayed on the host computer's terminal 24 when the user starts processing samples.

Storing Data On The Fixed Disk

All the above categories of data are stored on the fixed disk in the host computer. The fixed disk provides extensive storage capability.

Working with the fixed disk is considerably more convenient than using floppy disks. The user doesn't have to remove and insert multiple disks, as one does with floppy disks, and the user can store very large files without having to worry about exceeding the storage capability of the floppy disk.

The host computer 20 includes two floppy disk drives, but these are primarily used for backing up the information stored on the fixed disk.

Other Forms Of Information Storage

The system has extensive, but not unlimited storage capability. Most blood banks process large quantities of information, so data is only stored on the fixed disk as long as it is needed.

Some information remains valid over the long term. For example, parameters like the test format are probably changed rarely, if ever. This information is kept on the fixed disk on a permanent basis.

Other information must be updated at regular intervals. For example, every time a reagent lot changes, the plate reader must be recalibrated and a new histogram generated for that test. The current version of this information is always kept on the host computer's (hereafter referred to as the host computer 20) fixed disk.

The test results the system generates are stored on the fixed disk as testing progresses throughout the day. At the close of the day this data is usually transmitted to a mainframe computer or copied onto floppy disk for permanent storage. These automatic procedures make space on the fixed disk for the next day's test results.

The fourth category of information, test status, has only temporary validity. Accordingly, it is kept on the fixed disk in its current form, but there is no need to archive it onto the mainframe or floppy disks.

Printing Reports

It is crucially important to have hard copy versions of many types of test and quality control reports. The system enables the user to produce a wide range of printed reports automatically, usually just by pressing a key on the host computer 20 keyboard. The user specifies the formats for the types of reports the user's facility generates. On command, the system automatically generates all pages, or selected pages of the reports the user request.

Accountability

Log-On and Log-Off

In a clinical setting like the blood bank, it is important to be able to establish which laboratory personnel were responsible for particular test operations. The system facilitates accountability several ways.

Only one person at a time can work with the system. The user "logs on" to the system when the user begins to use it, and "logs off" when the user is done. One does so by identifying oneself to the host computer 20, typing in the users initials and a designated password. The user's initials are then printed automatically on the record of samples that are processed while the user logged onto the system.

Manual Data Entry

Whenever information is entered manually, or is edited through keyboard input, or whenever a sample is retested, the laboratory report forms indicate these procedures in a special column on the printed page. This arrangement increases accountability for work done with the system.

Double Keying of Data

The system was designated to accommodate the double key procedure some facilities use to increase the accuracy of manual entry of crucial information. First, the user types in the values, then the screen goes blank, and the user types in the values a second time. If the two entries match, the system accepts this as valid input. If there's a discrepancy the user is notified immediately, so that the user can correct the error.

Levels of Access

When the user logs on to the system, the password the user types in identifies the system functions the user is authorized to work with. The system has three access levels. Level 1 is the most restrictive, level 2 is less restrictive, and level 3 allows access to all system functions.

The Technician who runs the tests on a daily basis has access to level 1. The system Supervisor has access to level 2, and the system Director has level 3 privileges. Individuals at all access levels can display and print daily test results. Only those with level 2 or 3 access can manually change ABO/Rh test results. Only those with level 3 privileges can change the threshold values that determine how data points from the plate reader will be converted into blood grouping results.

USING THE PROGROUP LIQUID-HANDLER

Overview

The ProGroup TM automated blood typing system System provides a wide range of liquid-handling capabilities. This system was designed as a dedicated instrument for blood typing and grouping. If the user chooses, however, he can also use the ProGroup TM automated blood typing system's liquid handler for other analytical procedures: ELISA wash, plate-to-plate transfers, plate-empty-fill, etc. These other capabilities are described in the ProPette Manual that is incorporated herein by reference.

This section describes the most important features of the liquid handler 26 (hereafter the liquid handler), and explains how these are used in ABO/Rh testing and antibody screening.

Overview of ProGroup Liquid-Handler

Referring again to FIG. 2, the ProGroup TM automated blood typing system liquid handler has four heads that perform specialized kinds of liquid transfer:

an X,Y head 28 (hereafter the X,Y head) for transfers from tubes to individual wells in a microplate, a 12-channel head 42 (hereafter the 12 channel head) for transferring multiple reagents to one or more rows of wells, a wash head 44 (hereafter the wash head) for procedures like ELISA wash, and a manifold 46 (hereafter the manifold) for rapid plate washing and filling.

The liquid handler includes a two peristaltic pumps 50 and 64, one feeding the wash head, and the other feeding the manifold.

The ProGroup TM automated blood typing system liquid handler makes transfers among several containers: a block 62 that holds multiple reagents and disposable tips, a block 60 with diluent and 48 wells for mixing, 96-well microplates 56 and 58, and a carousel 20 of 13×100 mm evacuated blood containers. The blocks and microplates are placed in a template on the liquid handler table 84 (hereafter the table). This movable table positions the appropriate row of the container beneath the head that is operating in that procedure. A plate stacker (not shown) delivers ABO/Rh plates onto the table for processing, then back into the rack on completion of the liquid-handling.

The carousel has a capacity of 48 tubes and disposable tips. The carousel rotates past a bar code reader (not shown), and within range of the liquid head that makes transfer from tubes to plates. Another bar code reader scans the bar code on the microplates.

The user uses a hand-held controller to enter certain values and commands, and to view some information.

LIQUID-HANDLING UNIT OVERVIEW

LIQUID DELIVERY OPTIONS

Fusion Head

The ProGroup TM automated blood typing system incorporates four methods of liquid transfer. All four heads are mounted permanently and operated under software control.

X-Y Head

The X-Y head is positioned at the left of the instrument. The X-Y head travels along a shaft that runs from left to right across the instrument. This head picks up a long disposable tip from the carousel, aspirates sample from the tube that has been rotated into the correct position, then moves gradually across the microplate, delivering sample to the specified wells in a given row.

X-Y Head and Liquid Level Sensing

The volume of sample in a tube can vary substantially. It is important to be able to determine the liquid level in each tube very precisely, to ensure that the tip is lowered to just the right height to pick up first only donor plasma and then only donor cells.

The ProGroup TM automated blood typing system uses a special liquid level sensing technique that locates the meniscus in each tube with great accuracy. The instrument has a hollow piston with a block driving a plunger up and down. When the tip is lowered into a test tube the plunger block is pushed down, forcing out the air in the tip. The pressure rises sharply when the air contacts the surface of the liquid. The air contacts the surface of the liquid. The pressure transducer registers this sudden increase, and this information allows the system to calculate the position of the meniscus.

When the liquid handler is aspirating plasma for the antibody screening plate or ABO/Rh plate, the end of the tip is placed just 1/16" below the meniscus. The height of the original meniscus and the setting for the hematocrit level enable the system System to calculate the height of the red blood cells in the tube. So, as long as the tube contains at least a certain amount of sample, when the liquid handler tip withdraws sample for transfer to the forward testing wells, it will aspirate only red blood cells.

After depositing the cells in the appropriate wells, the X-Y head ejects the used tip into a receptacle at the right side of the table. It then repeats this cycle. Transferring sample from eight donor to a 96-well plate takes about 30 minutes.

Fusion Head

The fusion head provides the mounting for the 12-channel head, the wash head and the manifold. The 12-channel head delivers from 1 to 12 reagents simultaneously to a row of wells on a microplate. The microplate can be moved steadily forward for rapid filling of one row after another.

12-Channel Head

The 12-channel head starts by picking up a row of short disposable tips from the reagent block at the back of the liquid handler table. The head then aspirates the desired reagents for a row of wells in this block.

Next the table moves the first row of the ABO/Rh microplate or the antibody screening plate under the 12-channel head. The tips are lowered until they are above the meniscus of the wells and reagent is dispensed into the wells without contacting the surface of the liquid they contain. This sequence is repeated until the entire plate is filled. The tips are not contaminated in the process, and they are replaced in the reagent block when the reagent transfer is complete.

Wash Head

The wash head is mounted in the center of the fusion head. The wash head allows the user to cycle substantial amounts of liquid through a row of wells.

Each of the 12 separate wash cannula groups consists of three cannulas pointing into the well, all at different angles. One stainless steel cannula pumps solution into the well, another keeps the well from overfilling and the third drains the well. Each set of cannula has its own sensing apparatus and operates independently. This mechanical and electrical configuration enables the liquid handler to cope with considerable variability in the amount of fluid the wells contain initially. No matter how full they are to start with, none will be overfilled in the wash process.

Wash Head Operation

The user can program the system to pump anywhere from 10 ul to 10 ml through a well in a continuous washing action, and to pump the well dry at the end, leaving no more than 3–4 ul behind. It is also possible to use the wash head to add liquid, stop for incubation, then use the wash head to suck the well dry again, all under software control. The wash head is designed for use in operations like the ELISA wash used in HTLV III testing.

Manifold

The manifold is used to wash and rapidly fill wells with diluent.

Pumps

The system liquid handler includes two peristaltic pumps. The pump 50 feeds the manifold for rapid plate filling and dilution. Pump 64, beneath it, feeds the wash head.

The pumps are primed simultaneously, under software control. They dispense diluent into the predilution block that is positioned near the back of the liquid handler table.

PREDILUTION BLOCK

Predilution Block

The predilution block is a container with a trough at the back. The trough holds the diluent, either saline or saline bromelin solution that is used to dilute the donor cells to the desired concentration. The system uses reagent cells in a dilution of about 1:3. The optimal dilution is established for a given lot of reagents, then the donor blood cells are diluted to the corresponding ratio.

Diluting Donor Cells

At the front of the predilution block are 4 rows of 12 wells. The manifold prefills these wells with 900 ul of diluent. Later the X-Y head aspirates donor cells from the tube, and delivers the aliquot of cells to the appropriate well in the predilution block. Since the X-Y head uses a tip to pipette donor plasma first, the tip is precoated before it picks up the donor cells. The result is that very few cells stick to the inside of the tip, a problem that often occurs with manual dilution of blood cells.

The cells are mixed with diluent by sucking in and blowing out the tip repeatedly as the tip is raised. This procedure mixes the fluids thoroughly, with a minimum of cell damage.

The diluted cells are then pipetted into the forward testing wells of the ABO/Rh plate.

REAGENT BLOCK

Reagent Block Functions

The reagent block is a container with two rows of wells that hold various reagents and two rows of short disposable tips. The back row of tips and the back row of wells are used to fill the antibody screen plate with one, two, or three types of reagents. The front row of wells and tips are used to deliver up to 10 different reagents to the ABO/Rh testing plate. The reagent block is refilled after every two carousels of samples have been processed. The block is washed and the tips are discarded at the end of every day.

If the user is performing the full range of ABO/Rh tests, the reagent block contains 2.5 ml each of the following:
immunoglobulin solutions for forward tests
Anti-A
Anti-B
Anti-A,B
Anti Rh
Bovine Serum Albumin
Cell suspension solutions for reverse tests
A1
A2
B
Saline solution

Using Reagents with ProGroup TM Automated Blood Typing System

The cell suspension reagents and antisera, and the antibody screen reagents are most effective in the ProGroup TM automated blood typing system at lower concentrations than the manufacturers provide. The user establishes the optimal dilution ratio using the procedure of option 140 on FIG. 3. This dilution ratio, the lot number, the expiration date, and the length of time a given lot of reagents has been used in the system are all included in a screen display that can be viewed on the host computer 20 or printed for inclusion in laboratory records.

Daily quality control procedures indicate whether each of the reagents is continuing to produce absorbance readings in the acceptable range. This information is provided in both tabular and graphic form in form of a Lange-Levy graph displaying daily absorbances for the reagents plotted with the absorbance on the Y axis and the day on the X axis for easy interpretation. This feature is embodied in the procedure of steps 202, 204 and 206 on FIG. 5A.

Step 202 represents the information screen given the user on the procedure used for non bromelin pretreated reagent cell suspension quality control procedures. Step 204 gives the procedure for quality control reagent cell suspension checks telling the user to place 3% BSA solution in the carousel test tubes instead of actual samples from donors to guarantee an emulated negative reaction. Step 206 tells the user the procedure for reagent handling for the reagent cell suspension quality control procedure. One of the things the user is instructed to do is to make sure the file 2 is displayed on the handheld controller of the liquid handler before starting this procedure. This causes the liquid handler microprocessor to label the bar code of the plates being processed in this procedure with a reagent cell suspension tag. This is recorded by the host in the look up table so that when the bar code from the same plate comes in from the plate reader, the host can look up the bar code and will know that the absorbance data from this plate must be stored in the reagent cell suspension quality control file. The data in this file is processed by the host in such a manner so as to be displayed in graphical format as shown in FIG. 15. Step 164 of FIG. 5A represents the process of receiving the absorbance data at the host, storing it and processing it for display as the QC chart. The process of displaying the QC chart is symbolized by block 167. Step 164 also displays the means absorbance and the maximum and minimum absorbances observed from the wells read for each different type of reagent. Block 168 is an information screen which tells the user the procedures that should be followed to bring the reagent cell suspensions back within accepted tolerance.

MICROPLATES

Plate Types

The ProGroup TM automated blood typing system enables you to work with 96-well microplates that are disposable or reusable. They can have a U-, V-, or flat-bottomed configuration. And they can be Cetus microplates, or micro-plate manufactured by another vendor. For consistent results, however, plates of a single type from a single source must be used.

If Cetus microplates are being used, the system automatically calculates the volume of the wells. If microplates from another manufacturer are being used, a special procedure must be carried out that allows the system to calculate the well height. This procedure is explained in the Cetus Pro/Pette Manual which is incorporated by reference.

Plate Usage

The system liquid handler processes two plates at a time. The liquid-handling for ABO/Rh testing is performed on the plate at the front of the liquid handler table, and the liquid-handling for antibody screen testing is carried out on a plate in the middle of the table.

If the ProGroup TM automated blood typing system is being used to perform the liquid-handling for Hepatitis and HTLV III testing, the handler works on pairs of plates.

The microplates and the reagent and predilution blocks are positioned within a set of rails or positioning guides on the liquid handler table. The user only changes the positions of these guides when there is a need to check the titer of the reagents used for antibody screening.

Plate Stacker

The plate stacker consists of two storage hoppers that hold a total of six ABO/Rh plates. The plate stacker mechanism removes a completed assay plate from the table and loads it into the bay of finished plates. Then a fresh plate is lowered to the level of the table and advanced onto the table by belts forming a conveyor. Each plate holds sample from eight donors. Thus, the six-plate capacity of the stacker matches the 48-tube capacity of the carousel.

The plate stacker does not handle antibody screening plates. These are put in and taken out manually. The liquid handler controller prompts the user to remove the antibody screen plate when it is ready for testing.

CAROUSEL

Tube Features

The carousel holds up to 48 tubes of sample and an equivalent number of long disposable tips. The tubes must be bar-coded. The Becton Dickinson Vacutainer (R), Terumo Venoject (R), Sherwood Medical Monoject (R) or comparable blood collection tubes are suitable for use with the system.

The tubes should contain between 2 ml and 9 ml of sample. The donor sample is anticoagulated plasma prepared by standard blood bank procedures.

Carousel Loading

The system uses long disposable Cetus Pro-Group tips. These are loaded into the carousel before the tubes of sample are inserted.

The tubes should be loaded into the carousel with the bar code at the top facing the outer edge of the carousel, so the code is visible to the scanner. The #1 is printed on the carousel to indicate the position of the first tube. Subsequent tubes are inserted in a counterclockwise sequence, as shown below. The carousel rotates clockwise to bring the tubes and tips within range of the X-Y head.

More than one carousel accompanies the system, so you can prepare the next group of samples while the system is carrying out the liquid-handling on the current group. When the user is ready to process a new carousel, it is installed on two aligning posts in the motor drive mechanism for the carousel.

If a carousel contains fewer than 48 samples one enters the actual number of tubes using the liquid handler controller. This prompts the system to stop processing samples after finishing work with the last tube present.

BAR CODE READER

Two Bar Code Readers

The system liquid handler includes two identical bar code readers. One at the left side of the instrument reads the bar code on each sample tube. The other at the right side of the unit reads the bar code on the microplates.

Function of the Tube Bar Code

The 7-digit bar code on the sample tube is the basis for the Whole Blood Number that identifies the sample. The liquid handler reads the bar codes on a group of eight tubes, pipettes the sample in these tubes, then reads the codes on the next group of eight tubes. The bar code, together with the carousel number and the position in the carousel identify each tube. This information enables the user to locate the tubes that require DU testing, or need repeat liquid-handling or other attention.

If the scanner cannot read the bar code on a particular tube, the system does not carry out liquid-handling on that sample. Instead, it skips the tube, and includes that carousel number and position on a list of exceptions. The tube can them be moved to a new carousel to see if this solves the problem. If the system is still unable to read the bar code the user can do the blood grouping and typing manually, and enter the results into the system through the system option 170 in FIG. 3.

Plate Bar Code

The sample destination is identified in terms of plate number and row number. This information enables one to locate a given row of wells if one needs to recheck the test results for any reason.

The bar codes on the ABO/Rh plate and the antibody screen plate are read as part of the automatic Homing and Priming operation at the start of the liquid-handling sequence. The liquid handler table moves rapidly back and forth, homing all the stepper motors in the unit and running the plates in front of the scanner.

LIQUID HANDLER CONTROLLER

Controller Function

The system liquid handler includes a hand-held controller with a LED display and a 19 character membrane keyboard. This controller is primarily used for functions like Plate-Empty-Fill and Well-To-Well transfer that are not an integral part of the blood testing process. If the user wants the Liquid-Handler to carry out any of the operations described in the Pro/Pette manual, he programs the instrument as described in that manual which is incorporated by reference herein. The user responds to prompts on the controller display by giving commands and entering values through the keyboard.

The Controller and The System Manager

When using the system liquid handler for blood grouping and typing, the user programs the system almost entirely through the host computer 20, as described in this manual. There are several operations (such as pushing the START key when ready to begin the liquid-handling on a new microplate) when using the hand-held controller. The other blood testing situations when the controller is used are:

homing and priming the pump (when a key on the controller is pressed to initiate the process), checking the titer of reagents for the antibody screen tests (when the Plate-to-Plate transfer capability is used to carry out a serial dilution using the controller fairly extensively), establishing tip height, when user is using non-Cetus microplates, and must establish the volume of the wells, and The controller is an important adjunct to the host computer 20, but the latter programs and controls 99% of the operations involved in grouping and typing blood.

LIQUID HANDLING FOR ABO/RH AND ANTIBODY SCREENING

Operating Procedures

The liquid-handling for blood typing and grouping consists of the following sequence of steps:

At the start of every other new carousel the user should do the following steps.

1. Fill the reagent block with 2.5 ml volumes of diluted reagent mixtures that have reached room temperature after being refrigerated.
2. Place of diluent in the predilution block.
3. Insert the Micro-Trof to catch the diluent that will be flushed through the system in the priming procedure.
4. Fill the carousel with up to 48 bar-coded tubes and a corresponding number of long tips.
5. Press the RUN key on the hand-held controller to start the automatic Home-Prime Pump procedure.
6. Press the STOP key when the diluent being pumped through the system has flushed out the tubing.
7. Empty out the Micro-Trof and put it aside.
8. Put the reagent and the predilution blocks into position on the liquid handler table.
9. Place the carousel on the bed with the #1 position corresponding to the active position for the X,Y head.
10. Load the plate stacker with six empty bar-coded microplates for ABO/Rh testing.
11. If necessary, manually insert a fresh plate for the antibody screen test.
12. Respond to the prompts on the controller display to enter the number of tubes in the carousel.
13. Press the START key on the controller.
14. The liquid handler manifold fills the wells of the predilution block with the appropriate quantity of diluent for the donor cell suspension.
15. The liquid handler reads the bar codes on the first eight tubes in the carousel.
16. The X,Y head picks up the first long tip from the carousel and pipettes donor plasma into 1, 2, or 3 wells of the antibody screen plate.
17. The X,Y head then returns to aspirate more donor plasma and places it in the reverse testing wells of the ABO/Rh plate.
18. Next the X,Y head transfers donor cells into the appropriate wells of the predilution block. The cells and diluent are mixed, then the resulting cell suspension is pipetted into the forward testing wells.
19. The X,Y head then ejects the used tips into the waste receptacle.
20. Next the X,Y head picks up the next fresh tip and pipettes plasma and cells from the next tube, repeating the above sequence.
21. This process is repeated until the first group of eight samples has been pipetted into the microplate.
22. The liquid handler then uses the 12-channel head to pick up the appropriate number of short tips from the front row of the reagent block.
23. The 12-channel head then aspirates aliquots of reagent from the front row of wells on the reagent block, and fills the ABO/Rh plate with these reagents.
24. The 12-channel head then returns the tips to the back row of the reagent block.
25. If all the wells on the antibody screen plate are now full, the 12-channel head also picks up the back row of tips from the reagent block.
26. The 12-channel head then aspirates reagents from the back row of the reagent block, and fills the entire antibody screen plate.
27. The tips in the 12-channel head are then replaced in the reagent block.
28. The plate stacker then removes the finished ABO/Rh plate from the table and loads it into the full plate storage hopper.
29. A fresh ABO/Rh plate is rolled out of the plate stacker and onto the table.
30. If the antibody screen plate is complete, an audible "beep" and a message on the controller display prompt you to remove the plate manually and put in a fresh plate.
31. At this point the system is ready to begin the liquid-handling on the next group of eight samples.

USING THE PROGROUP PLATE READER

Overview

This section describes the major features of the system plate reader 28 and how it operates in context of the system.

Plate Reader Functions

The system plate reader measures the optical density, by way of absorbance, of solutions in the wells of 96-well microplates. In the context of the system the plate reader makes two off-center readings for each well using a single wavelength.

Plate Reader Technology

A tungsten halogen lamp provides light that is collected and passed through a narrowband filter with a wavelength of 410 nm. The filtered light beam illuminates the large end of a fiber-optic bundle. Light from the 12 fiber ends passes simultaneously through the bottom of all 12 wells in a row, and exits from the top of the wells. Then it falls onto the surface of 12 photodetectors.

The photo-detectors provide an electrical signal that is directly proportional to the amplitude of the light. This linear electrical signal is converted to optical density units using a logarithmic amplifier. The output voltage from the logarithmic amplifier is in turn converted to a digital value. The actual optical density of a row of wells is computed relative to a blanking well designated by the host computer 20, i.e., the Bovine Serum Albumin containing well.

A custom programmed EPROM (Erasable Programmable Read Only Memory chip commercially available) added to the plate reader permits very precise control over the motorized carrier that positions the plate in relation to the light source. This firmware allows one to calibrate the plate reader to make two off-center readings of each well in the positions that provide optimal differentiation between positive and negative test results.

PLATE READER FEATURES

Performance Specifications

The plate reader reads all 96 wells in a microplate in approximately 60 seconds. The measurement range is 0.000 to 2.999 Absorbance Units over wavelengths that can range from 380 nm to 750 nm. The narrowband interference filters are mounted on a wheel with a capacity of six filters. The linearity is plus or minus 1% of the best straight line approximation from 0.000 to 2.000

O.D. The combined accuracy and repeatability is plus or minus 1% and plus or minus 0.010 of the true optical density relative to air on the absorption peak of the solution at a single wavelength. Successive readings of a well produce results that are repeatable within plus or minus 5% and plus or minus 0.005O.D., when measurements are made at a single wavelength and blanked on air.

Plate

The Bio-Tek plate reader used in the system System can operate in a variety of modes. You can program it directly, using the 31 character keyboard and the 16 character display that are built into the plate reader. You can also output data directly from the plate reader to a parallel printer.

In the context of the ProGroup TM automated blood typing system, however, the plate reader operates entirely under computer control of the host computer 20. This option allows the plate reader to accept commands from an external computer (in this case the host computer 20) and to transmit the optical measurement data it generates back to the computer, for analysis there. A serial I/O link permits the plate reader to operate in this fashion.

How the ProGroup Uses the Plate Reader

When using the plate reader for ABO/Rh testing, the instrument is calibrated and controlled through the ProGroup TM automated blood typing system host computer 20. The user gives the initial directive to start the plate reader by selecting the plate reader function on the host computer 20 terminal. After mounting the plate in the reader (as described below) you simply press the START key on the plate reader keyboard.

The readings are made automatically, and the optical density measurements are immediately transmitted to the host computer 20. There, the higher value is discarded and the lower value is stored on the computer's hard disk. The computer interprets this value in relation to user-defined thresholds that differentiate between positive, negative, and ambiguous test results.

The user can view these test results at his convenience on the host computer 20 screen by selecting the Results Summary function 190 in FIG. 3. Processing is then vectored to the process shown in the flow chart of FIG. 8 where the user can select which test results he wishes to review. If he wishes to view the results for a particular WBN, he selects option 201 and can have the results printed by selecting option 203. If he wishes to view the NTD list, he selects option 207. This produces a report of all the WBNs process on a given date defined by the user which produced no type determined results together with the carousel number and test tube position of the NTD tube in that carousel and the plate number and row number of the wells containing samples from the NTD tube. This use can be used to detemine which plates or sample tubes need to be pulled from storage for retesting or rereading. This list can be printed by selecting option 209. If the user wishes to view the DU list, he selects option 193. This causes the report generator routines in the host processor to generate a list of all the unverified Rh negative test results processed on a given data along with the carousel number and tube position for the tubes. This report may be used to determine which tubes to pull for further DU testing.

If he wishes to view the list of all WBN's of a specified group and type, he selects option 211. This report allows the user to search for all samples processed on a given, user defined date with a specified blood group and type. The report lists the WBNs in numerical order and gives the carousel number and tube position of each tube. This report may be used to identify which samples to pull to expedite testing of blood with a particular profile.

If he wishes to view the current test status, he selects option 213. This report gives the user an overview of how far testing for a given, user defined day has progressed. The report provides a count of the number of completed plates and the plates yet to be read, and provides a count of the NTDs and unverified Rh negative test results determined up until the time of the report. This report may be used to assess test status at any given moment.

If he wishes to view the directory of plate information, he selects option 215. The first screen of this report lists all plates processed on a given, user defined date and supplies the test status of whichever plate the user identifies as to whether the plate is tested or untested. The status of the plate is tested after it has been read in the plate reader even if the plate contains NTDs or Rh negatives that have yet to be tested for DU. The second screen in this report consists of a table of data on the plate identified by the user with the WBN for each row of samples together with the blood group and type for that WBN and the test status displayed. The test status is displayed as R for resolved, NTD for no type determined or H for Rh negative for which a DU result is not yet available. This report may be used to determine the test status of a plate, if, for example, the user cannot remember whether a particular plate has been read or not. The second screen of the plate testing status report is symbolized by block 217 in FIG. 8. A directory of antibody screen plates can be viewed by selecting option 219 which shows the WBN antibody screen results for the wells in the plate identified to the system in step 221. This report consists of a table of WBNs for all samples processed on a given date, with the results of testing for the antibody screens, and for any miscellaneous immunoassay tests performed on that WBN which have been done manually and entered into the system manually.

A display of all ABO/Rh testing totals can be viewed by selecting option 223. This report summarizes the number of units of each group and type of blood that were processed on a given date, and provides the total number of resolved samples, the number of NTD's, and a grand total of samples processed. Any tubes that were omitted from sample processing will be omitted from these totals. This report provides an overview of testing results.

The user can ask for and receive a report of the omitted carousel positions by selecting the menu option represented by block 225. This selection causes the report generator to collect and process the data regarding tubes that have not been processed and to generate a report that gives the carousel number and tube position for tubes that were not processed on a given date, together with the reasons for the omissions, e.g., a short fill, bar code error etc. The liquid handler 26 collects this information and sends it to the host for storage in a file dedicated to this type of information. As is the case for all the reports generated by the routines symbolized by FIG. 8, the omitted carousel positions report may be printed simply by selecting the menu option to print the report. All these reports can be generated in real time, i.e., while the user waits.

Information on test results is displayed in the type of template shown below. Instead of being given a series of optical density measurements, the following symbols, which represent results for individual tests, are shown:

P=Positive
N=Negative
?=Ambiguous results.

The user can reread a particular row of wells a second time, either automatically or by eye. If need be, the user can repeat the entire liquid handling and plate reading operations, either manually or automatically. The final results are entered into the system data base using the host computer 20 keyboard and display.

The user can print the test results using a function on the host computer 20. The user obtains a hard copy from a printer attached to the host computer 20, and the format for the report is predefined through the host computer 20.

OPERATING SEQUENCE

Using the Plate Reader

The user should read a plate no fewer than three and no more than ten minutes after the final resuspension for best results.

1. When the liquid handling on a plate is complete, select the plate reader function from the ProGroup ™ automated blood typing system host computer 20.
2. Position the plate, so the bar code is facing the plate reader keyboard.
3. Load the plate into the motorized carrier by tipping the front of the plate down slightly.
4. When the front of the plate is firmly seated push the back edge straight down to engage the spring.
5. Press the START key on the plate reader keyboard.
6. The motorized carrier will move the plate into the instrument and the shutter will close behind the plate. The plate reader displays the bar code that identifies it.
7. The first information obtained from the plate is the bar code that identifies it.
8. If you listen closely, you can then hear the sound of the plate being positioned for each of the 16 series of readings, and the clicking of small relays each time a measurement is taken.
9. The optical density, i.e., the absorbance information is then automatically transmitted to the host computer 20 for analysis and storage.
10. When the plate reading is complete, after about a minute, the shutter will open and the plate carrier will move back out to the starting position.
11. Remove the plate by first lifting up the back edge slightly, then disengaging the front end.
12. When the plate reader is ready to read another plate a message will appear on its display.
13. Repeat the above sequence.
14. To view the test results select the Results Summary function 190 on FIG. 3 through the host computer 20.

System Configuration

Figure 11:
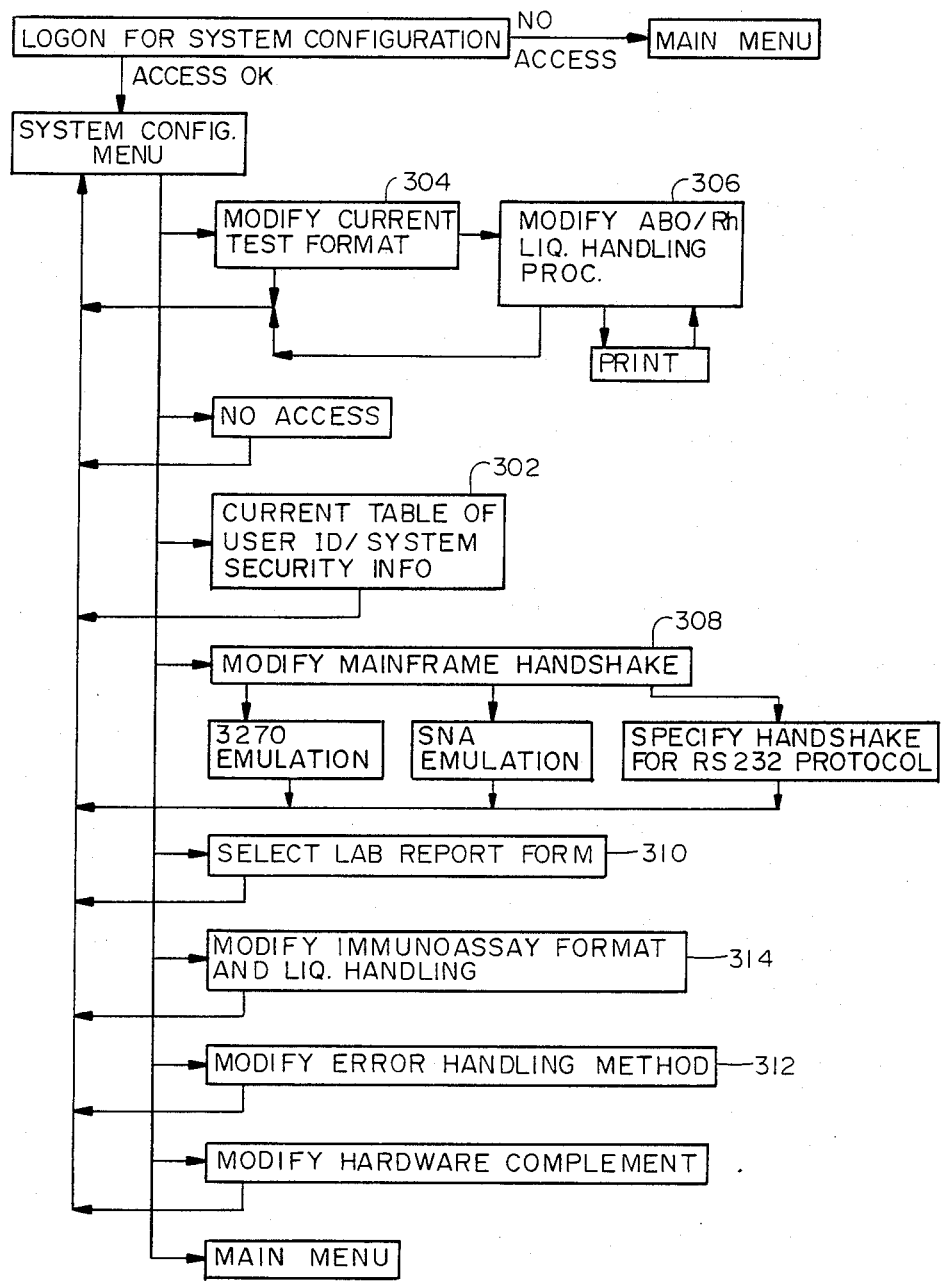
FIG. 11 is a flow diagram of the process used by the system in allowing the user to configure the system for a specific installation.

Certain functions of the system can be performed only by the system Supervisor or the system Director. These can be performed by selecting option 300 on FIG. 3 which vectors processing to the process shown on FIG. 11. For example if the format of the test for ABO/Rh is to be changed in that a different pattern of reagents or a different set of reagents is to be used, the system Supervisor can make that modification by selecting option 304. This allows the process performed by the liquid handler to be modified using step 306. If the handshake or protocol for information exchange with the mainframe needs to be modified such as when a new mainframe is connected to the system, the protocol may be changed by selecting option 308. Also the format for lab reports may be set up by selecting option 310, and the error handling method used by the system may be modified by selecting option 312. The liquid handling procedure for immunoassays may be modified by selecting option 314.

Reader Calibration

Reader calibration is a task which is important to the successful operation of the system. Blood group and type assays involve reacting donor red blood cells with antisera or antibody reagents (forward typing) and reacting reagent cells of known type with donor plasma (reverse typing). These reactions produce templates of positive and negative reactions to each of the various multiple reagents used on the blood of each donor. The template is comprised of a string of positive and negative reactions that define the blood group and type according to which reagents elicited positive reactions and which elicited negative reactions. The positive reactions are characterized by agglutination buttons in the bottom center of the test wells. The plate reader shines a light beam through the bottom of the well at an off center position that should clear the button and pass through the liquid with less absorbance if a positive reaction occurred than if a negative reaction occurred. The light absorbance readings from each well are then interpreted by the host computer 20 according to two thresholds. One threshold is the positive threshold which defines a light absorbance value that is the upper limit for light absorbance for a positive reaction. The other threshold is a negative threshold that defines the lower light absorbance limit for a negative reaction.

The invention allows the user to view histograms for the population of light absorbance readings for reactions to various reagents or donor cell suspensions or plasma blank and then to graphically adjust the positions of the thresholds based on the histogram graphic display. This reader calibration process insures good test result interpretation. The system automatically prompts the user through the process of doing the liquid handling for the control histograms (donor cell suspension and plasma blank) and the actual forward typing and reverse typing reagent histograms. Basically the host computer 20 performs the process of analyzing light absorbance data read by the plate reader from test wells containing donor samples that have been reacted with reagents and processing and storing the data and plotting histograms of that data. The user can then graphically locate the two threshold points which define positive and negative reactions by the values of absorbance on the histogram. These histograms are frequency distributions for the number of samples in the sample population of 48 or 96 which produced particular absorbance readings or absorbance ratios. On all the histograms, the Y axis indicates the total number of samples that had each absorbance or absorbance ratio. On the reverse typing and control histograms, the X axis shows the actual absorbance reading. On the forward typing histograms, the X axis shows the absorbance ratio between the test well and the cell suspension. FIG. 12 shows a forward typing histogram.

The first histogram in the series is the donor cell suspension histogram. It shows one group of readings which are clustered together in some are of the graph. The plasma blank histogram is similar in this respect in that it shows only a single distribution of absorbance values. These two histograms define the range of acceptable values for the concentration of cells in the donor sample and the optical properties of the donor plasma. It is necessary to define limits for these ranges to ensure some consistency between donor samples. When the cell suspension absorbance reading for a sample falls outside the acceptable range, all readings for forward typing tests for that sample are designated as questionable results. This prevents a very high or very low absorbance reading due to an excess or deficiency of cells in the wells from being confused with a genuine positive or negative test result. The plasma blank performs the same function. It screens out samples where the plasma bland well is very clear, indicating perhaps that little or no sample was delivered to the well, or very cloudy plasma, indicating perhaps that the sample is excessively lipemic. When the plasma blank absorbance reading for a sample falls outside the acceptable range, all readings for reverse typing tests for that sample are designated as questionable results. This prevents distorted absorbance readings from being interpreted as legitimate test reactions.

The histograms for the various reagents used in the forward and reverse typing tests have a different configuration. These histograms show two distributions of absorbances. One group of low absorbances generated by the positive sample readings and another group of high absorbances generated by the negative sample readings. These two clusters are separated by a buffer area. An example of such a histogram is shown in FIG. 12. One histogram is prepared by the host computer 20 for display on the terminal for each different reagent used in the forward and reverse typing. The user may then calibrate the plate reader by setting the positions of the thresholds by graphically moving the threshold arrows on the histogram display.

This calibration process is performed by selecting option 500 on FIG. 3 which vectors processing to the routine symbolized by FIG. 9. The user then logs on the reader calibration function, and the system checks his ID against the user privilege table to determine if this user may have access to this function. If access is granted in step 502, the reader calibration menu is displayed in step 504. This menu gives the user the option of determination and setting of proper threshold values or modifying stored threshold values or setting liquid handling procedures for determining plate reading positions or modifying plate reading positions.

Figure 9A:
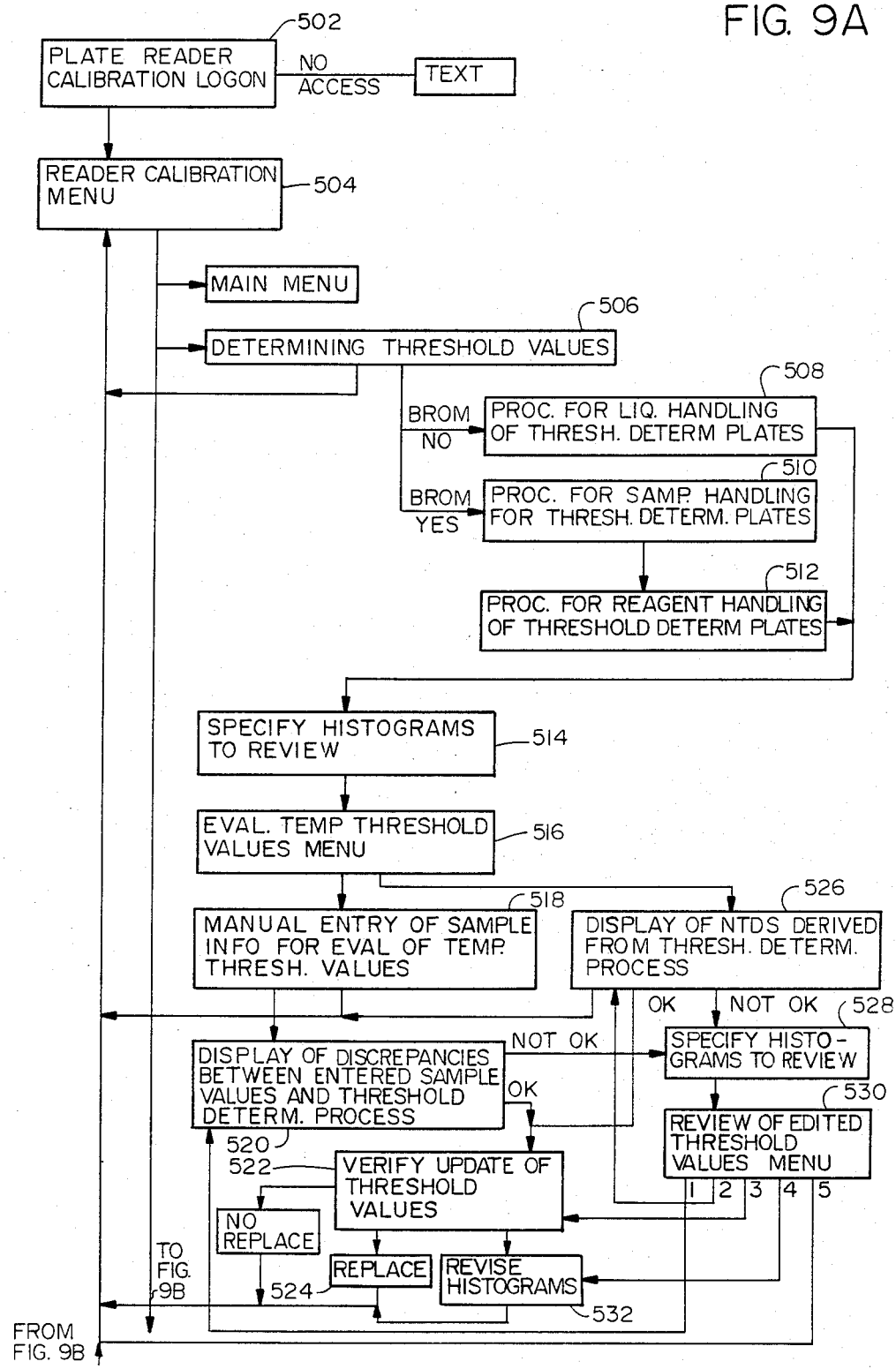
FIGS. 9A and 9B are a flow diagram of the process that the system follows in allowing the user to calibrate the plate reader and to adjust the thresholds used by the host computer in interpreting test results.
Figure 9B:
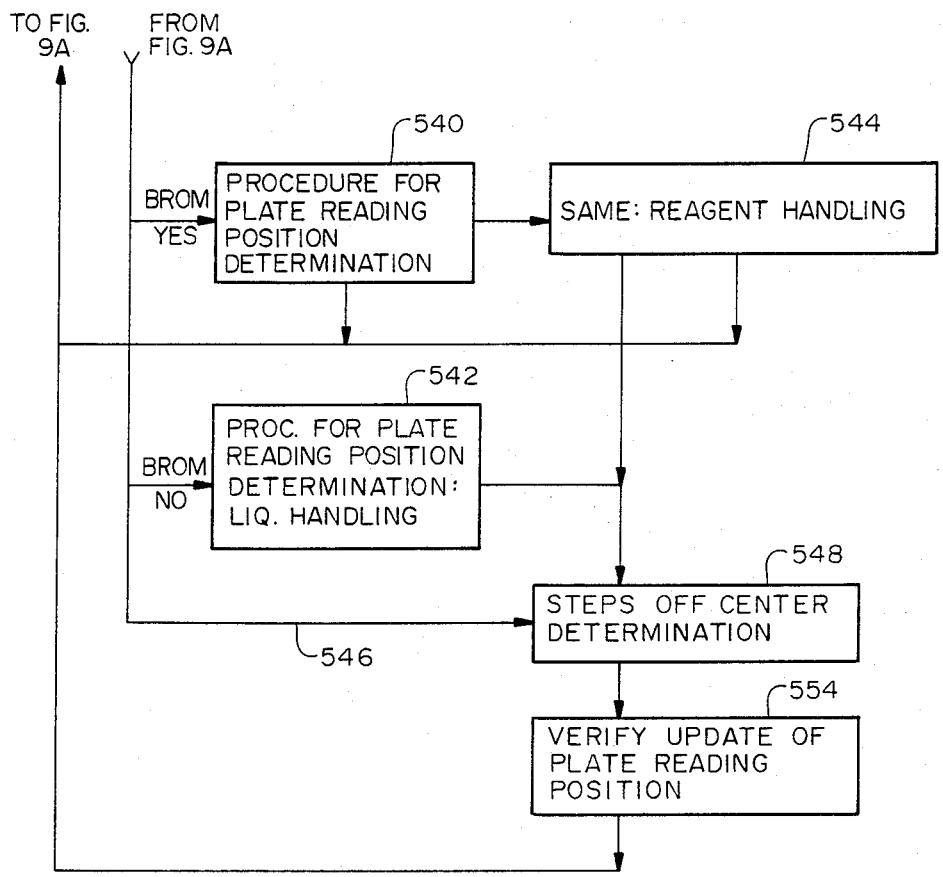
Figure 10:
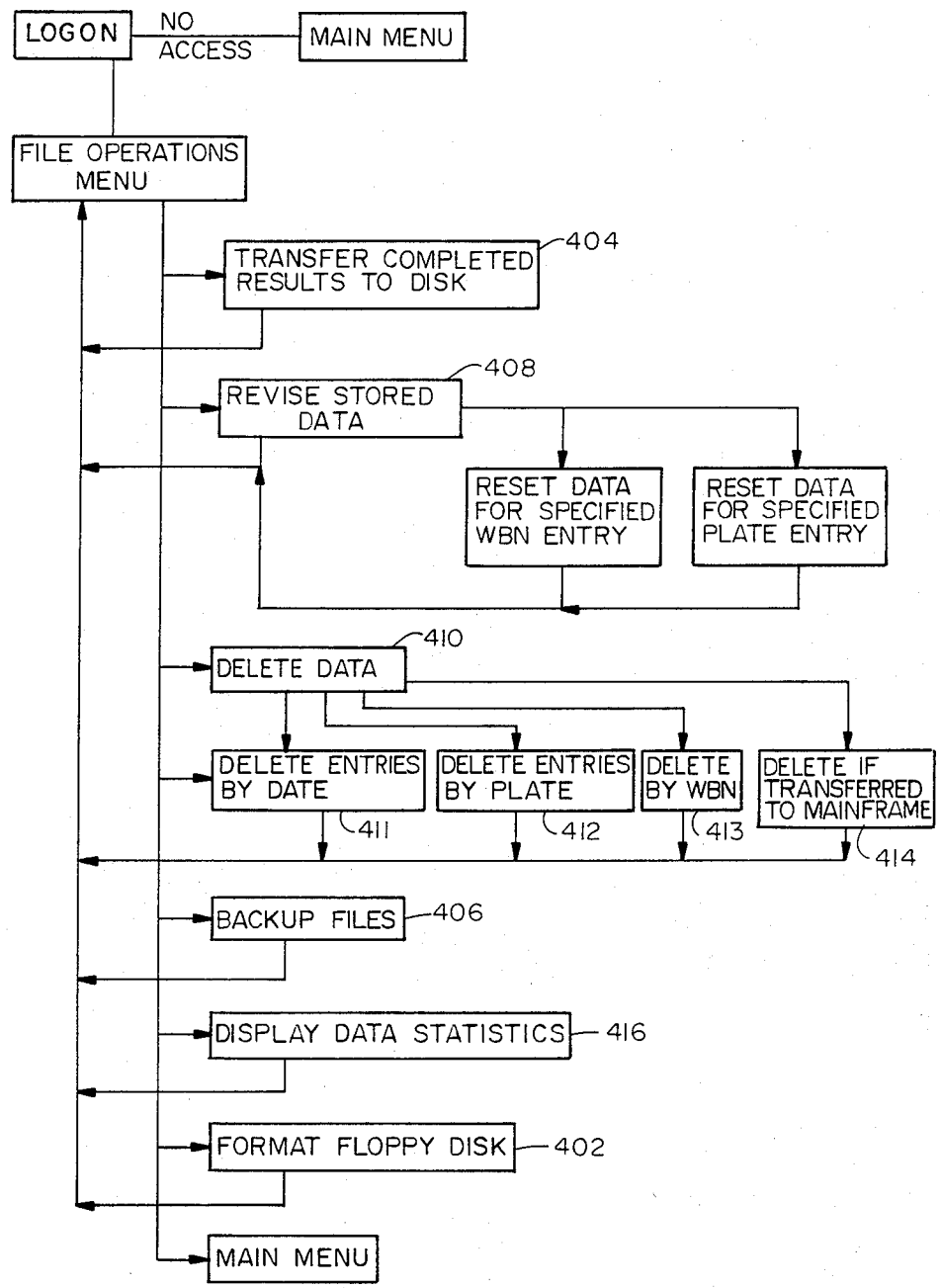
FIG. 10 is a flow diagram of the process used by the system in performing various file operations.

The option to set proper thresholds in histograms to distinguish between positive and negative reactions requires that the user select option 506 in FIG. 9A. The user is then instructed at steps 508 or 510 of the liquid handling procedure to use for sample handling for this process. Basically the user is instructed to fill 48 tubes having bar codes with donor samples of known group and type in a distribution of approximately 30% A, 30% O, 25% B and 15% AB. Two of the samples should be limpemic and two should be slightly hemolysed. The user is then instructed to use file 12 for control of the liquid handler. This file automatically prepares the donor cell suspension and the plasma blank. Step 508 gives the instructions for tests that do not use bromelin pre treatment, while step 510 gives instructions for bromelin treated samples. The liquid handling instructions for the reagents necessary to perform this process are then given in step 512 and information on how to set up the liquid handler is given. Then, 6-12 plates are processed in the instructed manner and are available to be read by the plate reader. The user then physically moves the plates to the plate reader where they are read using the plate reading positions defined above. The absorbance results are then automatically organized into histograms by the host computer with the percent of the total number of samples plotted on one axis and the absorbance of the sample plotted on the other axis. The horizontal axis is actually the observed absorbance divided by the absorbance of the cell suspension (bovine reagent setting maximum possible absorbance), i.e., the absorbance as a percent of the total possible absorbance. One histogram is prepared for each type of reagent used (anti A, anti B etc.). Such a histogram for a particular reagent is shown in FIG. 12. The arrows 517 and 519 represent the temporary thresholds which can be set by the user by manipulating the cursor movement keys on the host keyboard. That is the arrows 517 and 519 can each be moved left and right. FIG. 12 represents the statistical results of the processing of a large number of donor samples. The height of the lines represents the percentage of the total population of samples which had the absorbance represented by the horizontal position of each line. The horizontal position of each line represents the absorbance observed for the number of samples represented by the vertical line at that position, if any, as a percentage of the total possible absorption. A donor sample tested in the batch of samples for which FIG. 12 is a histogram, will be called a positive reaction if its absorbance readings is to the left of the absorbance threshold marked by the arrow 517. If the sample's absorbance is to the right of the absorbance threshold marked by the arrow 519, the sample will be characterized as having had a negative reaction to that reagent. If the absorbance falls between the arrows, the sample will be characterized as being NTD. The total number of NTD's for the current threshold settings is shown and updated in real time in a legend shown on the graphic display of the histogram as at 521 in FIG. 12. When the user changes the positions of the arrows representing the current positive and negative thresholds, the number of NTD's will be updated based upon the new threshold values. Also, the host displays the actual absorbance value for each position of the positive and negative threshold values. As the position of the thresholds is varied, the absorbance values at these threshold locations is given at 523 and 525.

When the user selects the menu option represented by block 506, the liquid handler attaches a "histogram" tag to the bar code of the plates processed according the instructions of screens 508, 510 and 512. When these plates are read by the plate reader, the absorbance data from these plates is sent to the host computer which collects it in a file for processing into the histogram data. Since a histogram is presented for each different reagent type, the liquid handler is loaded from the host with instructions as to which reagents to put in specific wells. The bar code information from the plates so loaded is then associated with the template of reagents for forward and reverse typing used for that plate. This allows the absorbance data coming from specific wells of a particular plate to be collected in the proper file for a histogram for each specific reagent. The host does this sorting by looking up the template of reagents used, i.e., which reagents were put in which wells, for the plate having the bar code sent by the plate reader. In other words, the absorbance data from all the A wells is collected and processed into histogram form, as is all the data from the B wells, the A,B wells and the Rh wells.

In step 514, the user specifies which of these above noted histograms he wishes to view, and the histogram is displayed graphically in a display like that of FIG. 12. The user is then allowed to move the threshold arrows, and the host stores the updated values for the positive and negative threshold values in a temporary file for each histogram. The user is then afforded an opportunity to review the results that will be obtained with the new threshold values to evaluate the new thresholds for quality control purposes. In step 516, the user is allowed to choose the manner in which he will evaluate the effectiveness of the thresholds he will set. His options are to evaluate the temporary threshold values by comparing experimentally determined data against data from known samples or checking the resulting number of NTD's that result from processing real donor samples.

If comparison to known data is selected, step 518 allows the user to type in the known data regarding the WBN and each blood group and type for each WBN. Once this is done, the discrepancies between the known data and the test results obtained using the temporary thresholds being evaluated are displayed in step 520. Blood typing requires the test results from all the different reagents to match certain known templates. Thus, step 520 represents the process of comparing the known template for the type of blood the system has been told by the user it is processing against the experimentally determined template derived using the histograms and thresholds established in step 514. The WBN of each manually entered known sample will be displayed and its known blood type will be shown next to it in step 520. The positive or negative reaction to each reagent will then be displayed in the row next to each WBN as determined from the new thresholds established in step 514 so that the user can compare the template for each sample which is experimentally determined using the temporary thresholds being evaluated against the known template for that type of blood. In this manner the thresholds can be adjusted to their proper values and the new thresholds set in the system via steps 522, 524 and 532. These steps overwrite the old threshold values with the new threshold values.

If the NTD approach is selected for quality control of the newly established thresholds, the step 526 displays the number of NTD's experimentally determined using the new thresholds. An NTD is determined by taking into account the positive and negative results to all the reagents using the new thresholds established in step 514. If the number of NTD's is acceptable, step 522 is performed to allow the user to update the old thresholds to the new thresholds established in step 514. If the number of NTD's is not acceptable in either step 526 or step 520, a step 528 is performed where the user is given the chance to specify which reagent histogram to review. Processing then proceeds to step 530 where the user has 5 options. He can review the effects of the edited thresholds by comparing the results of previously run samples with their entered known values which vectors processing back to step 520. He can review the effects of edited threshold values by checking the resulting number of NTD's which vectors processing back to step 526. He can decide to update all or some of the thresholds by vectoring to step 522, or he can refuse to update any thresholds and review the histograms vectoring processing to a step 532. Finally, he can go back to the menu of step 504.

The system allows different manufacturer's plates to be used in the plate reader. Different manufacturer's plates have different well bottom configurations. These different well bottom configurations cause different meniscus lens effects and other optical effects which can adversely affect the quality of absorbance readings unless steps are taken to adjust the operation of the system to account for the peculiarities of a particular plate.

The CPU 20 controls the plate reader to take multiple absorbance readings by shining a light up through the bottom of the well at a wavelength controlled by a command from the CPU 20. The beam is shined up through the bottom of the well at each of several angles both in the center of the bottom of the well and at positions off center. If a positive reaction bottom is settled in the bottom center of the well, the absorbance readings will be different at different angles. If a negative reaction exists, the absorbance will be more or less constant at all angles. Thus, the system can discriminate between positive and negative reactions. Therefore the best angle to take the absorbance readings must be determined to optimize the discriminatory powers of the system.

The menu option for setting liquid handling procedure for determining plate reading position displays screens of information which instruct the user to put known type O blood in 8 donor well positions. To these samples are added the proper reagents to cause positive reactions for anti-Rh and reverse typing reactions A1, A2 and B. These instructional screens are symbolized by the blocks 540, 542 and 544 in FIG. 9B, and the menu option is symbolized by the block 504 on FIG. 9A. The plate is then processed using the ABO/Rh testing procedure following the directions given on these screens.

The host CPU stores predetermined liquid handling routines for each different type of plate that will be used in the system. These routines are stored as files. When the user loads the liquid handler with a particular type of plate, the user will signal this fact to the host CPU by ordering from the handheld controller that liquid handling is to be done on that plate using the file designated for that type of plate. The host CPU then downloads the liquid handling machine instructions to the liquid handler 26. The liquid handler then reads the bar code on the plate and tags that bar code with a "steps off center" tag. This data is then sent to the host CPU and stored there in a look up table of plate bar codes.

When the plate is ready to be read, the plate is put in the plate reader. The plate reader reads the bar code of the plate again, and this is sent the host CPU 20 (hereafter called the host). The host then looks up the plate's bar code from the stored bar codes in the look up table and determines if the plate is a "steps off center plate". If the plate is a steps off center plate, and the user selects a menu option telling the host that the user wishes to adjust the plate reading positions of the two off center readings to maximize the discrimination between positive and negative reactions, then the host vectors processing on line 546 to a step 548 where specific commands are to the plate reader 28. These commands order the plate reader to set the wavelength of the light being used for the absorbance readings and orders the plate reader 28 to take 36 absorbance readings across each well bottom at each of 36 different positions across the bottom of the well. These absorbance readings are sent to the host from the plate reader. The host then performs some calculations on the data to prepare it for display, and then the data is graphically plotted with absorbance on one axis and angle of each reading on the other axis. The plot will show high absorbance readings at angles that pass through the positive reaction button in the middle of the bottom of the well. On either side of this button will be angles having low absorbance. FIG. 13A shows a typical well bottom with a positive reaction button and FIG. 13B shows a typical graph which results from this process reading process for a positive reaction button. Note the high absorbance for the readings taken where the beam passes through the center of the well bottom where the positive reaction agglutination button is located. The absorbance readings are lower for readings on either side of the positive reaction button in the center of the well because the light passes to one side of the button and not much is absorbed by the clear fluid as the light travels to the photosensitive detector above the well.

At angles that pass through points on the bottom very near the wells, high absorbance values will exist caused by the lens action of the walls and the bottom shape. Two arrows 550 and 552 are displayed. These arrows represent the current position of the two readings that are taken off center in addition to the readings taken in the center of the well bottom. These arrows can be graphically moved by the user through use of the arrow keys on the keyboard of the host 20. The positions of the arrows 550 and 552 define the step position or position off center at which the two off center readings are taken. After the user has viewed the graphs for each of the positive anti-Rh, A1, A2 and B reactions and selected the arrow positions for arrows 550 and 552 which present the best compromise to discriminate for positive reactions for each type of reaction, the host then records the arrow positions and verifies the user's desire to use these arrow positions for future readings in the step symbolized by block 554 in FIG. 9B. The host computer will then instruct the plate reader to use these angles for absorbance readings for these types of wells for all subsequent readings of all wells in ABO plates if the user instructs the host computer to replace the current angles with the newly selected angles. These reading positions are then used for all subsequent readings of these type plates including reagent and donor cell suspensions and histogram plates and quality control plates but not for immunoassay plates. More detail is given on this aspect of the invention and the other aspects of the invention in the CETUS PROGROUP SYSTEM USER'S MANUAL dated May 28, 1986 available from Cetus Corporation in Emeryville, Calif. which is hereby incorporated by reference.

Another major advantage of the system over the prior art is the ability to graphically fine tune the systems ability to discriminate between positive and negative reactions. This improves the accuracy of the system and reduces the number of NTD WBN's that result from processing a batch of donor samples. The graphic display allows the user to very quickly and easily grasp the statistical results from processing a batch of donor samples. This allows the user to graphically adjust thresholds which are used to discriminate between positive results, negative results and the NTD area. This gives the user a very powerful and effective tool to optimize the operation of the system.

Using the ProGroup System Manager

Overview

Since the user primarily interact with the host computer 20 through its software, this section focuses primarily on how the user works with the ProGroup TM automated blood typing system programs.

These application programs have been created specifically for use in blood banks. The software is quite self-explanatory.

System Manager Summary

Computer Features

The computer has a number of serial and parallel ports that allow it to interact with external devices in the system: the terminal, printer, liquid-handler, plate reader and orbital shaker. These devices are largely or entirely controlled through the computer and the data they generate is stored in the computer.

Terminal Features

The terminal consists of a monochrome (green) display with two modes: a standard matrix of 80 characters by 24 lines for conventional screens, and a high density matrix for screens that contain very large amounts of data.

The detached keyboard includes a set of standard typewriter-type keys, plus special keys for cursor control, the numeric key pad, etc. . Most of the function keys at the top of the keyboard are not used in the ProGroup TM automated blood typing system application.

System Manager Software

The Micro PDP/11 host 20 runs the commercially available operating system called RSX11 that enables the ProGroup TM automated blood typing system host computer 20 to carry on several operations at the same time. The operating system provides a set of standard operating system management processes to allocate the machines resources among the various tasks or applications running on the system. It also serves as an intermediary between the computer and terminal hardware and the application software.

The specific functions involved in typing and grouping blood are carried out by a group of application programs developed by the assignee. The reset of this section explains how these application programs are structured, and how the user interacts with them.

ProGroup Application Programs

Application Program Design

ProGroup TM automated blood typing system facilitates the work by using the terminal screen to:
list all the options at any given point in the program,
summarize the steps in each procedure such as setting up the liquid handler for quality assurance or sample testing,
giving the user on-screen help to remind the user what keys the user can use at any given time, and
providing a status line for other relevant information, such as error messages or a brief explanation of the task the system is performing.

Interacting With The System Manager

The user interacts with the host computer 20 in two basic ways:

by supplying new information, or updating data that is already stored in the computer, or by directing the system to carry out a particular kind of task.

The user performs these two types of operations in a similar way. First, the user moves the cursor to the appropriate point on the screen. The cursor location shows where the next alpha-numeric character the user types will be placed (if the user is entering or editing data) or which option will be selected out of a list of alternatives (if the user is designating a task). The user moves the cursor around the screen using the arrow keys at the right side of the terminal keyboard.

If the user chooses a task from a list, one simply presses the return key when the cursor is in the right spot. If the user is entering or modifying data, the user types the character or digit, then press the Return key when the entry is complete. Pressing the Return key tells the computer to act on the input.

Working with the ProGroup TM automated blood typing system host computer 20 is simply a matter of repeating these two kinds of operations: first to program the system to perform the blood grouping and typing procedures in a particular fashion, and then to run these tests and quality assurance procedures on a daily basis.

Controlling ProGroup Activities

Multi-Tasking Software

The host computer 20 controls the ProGroup TM automated blood typing system liquid-handler, plate stacker, bar code reader, plate reader, orbital shaker, terminal and printer. The user gives directions to the computer and it, in turn issues instructions to all these devices. Because the ProGroup TM automated blood typing system has multi-tasking software, the computer can control a whole range of activities simultaneously. The ProGroup TM automated blood typing system can concurrently:

perform the liquid handling on six plates of sample (including automatic insertion and removal of ABO plates and bar code reading on both ABO and antibody screening plates), read the optical absorbance results on a series of plates as they are inserted and remove them from the plate reader, print a designated document, such as a list of NTDs for the day's testing, and allow the user to interact with the ProGroup TM automated blood typing system programs or the data stored in the system, for example, to edit the test results for a WBN, or to check the status of testing on a given carousel of samples.

Once the user has directed the host computer 20 to start a particular task (such as liquid handling on a stack of plates) the computer will carry that operation through to completion. With that task under way, the user can use the terminal to select and initiate another function (such as printing a given document). In this way, the user can use the computer to execute multiple tasks "in the background", while the user interacts with the terminal "in the foreground".

Selecting A Function

The various ProGroup TM automated blood typing system functions are grouped into lists of options. These lists are known as menus. The menus are organized into the hierarchy shown on the next page: from the most general choices on the first, or "main" menu of FIG. 3, to the more specific choices on the subordinate menus of FIGS. 4-11.

When the user selects a menu option (by moving the cursor to that point and pressing the Return key) that indicator is highlighted for a moment, then the appropriate screen appears on the display. Often, the next screen is another menu, showing the alternatives within that overall category.

Menu Arrangements

Vertical Menus

Higher level ProGroup TM automated blood typing system menus are vertical lists of up to nine options, as shown below. The only information that appears on these screens are the menu choices.

Horizontal Menus

The lower level menus include several options listed horizontally across the bottom of the screen. These menus are included on screens that present program data of various kinds. Printing is a function that always appears on this kind of low level horizontal menu.

Selecting Menu Options

Making Choices

Both vertical and horizontal menus respond in the same basic fashion.

1. use the right and left arrow keys to position the cursor at the option the user is choosing. The right arrow key moves the cursor to the right or down. The left arrow key moves the cursor to the left or up. The up and down arrow keys do not move the cursor when the user is working with menus.
2. When the cursor is in the right spot, press the Return key.
3. The indicator for that option will be highlighted momentarily, then the next appropriate screen will appear on the display.

Entering And Editing Data

Typing Input

The other major way the user interacts with the Pro-Group TM automated blood typing system host computer 20 is by typing in data for the system to act on. Sometimes this is a fill-in-the-blank operation. At other times the user supplies information as part of a list or table.

In both cases, the user follows the general sequence given below:

1. Position the cursor at the spot on the screen where the user wants to place the first character the user will input.
2. Type in the appropriate sequence of alpha-numeric characters and spaces. These will appear on screen as the user enters them. The user can type upper or lower case characters, as both are acceptable.
3. In most cases the user presses Return after each individual entry.

4. The cursor then moves to the next position where data can be entered or modified, and the user repeats the process.

The information the user gives the ProGroup ™ automated blood typing system host computer 20 serves one of the following purposes:
  providing new data,
  modifying existing data, or
  altering a default value.

Entering New Data

In many situations the host computer 20 requires input from the user to carry out a task. For example, when the user wants to check the test results for a particular WBN, the user must type in the digits that identify that sample. The position for the entry is indicated by a colon after the heading, or by a pair of brackets.

Modifying Data

Alternatively, the user may be revising data that is already stored in the computer. For example, if a given sample was originally categorized as NTD, certain individual test results must be changed after the blood group and type have been positively identified. In this situation, the user is typing over some or all of the data that already appears on the screen. The user changes the screen by:
1. Placing the cursor in the right spot,
2. Typing in the appropriate characters or pressing the space bar to create a blank, then
3. Moving the cursor to the next location that requires a change.

Changing Default Values

In some situations the ProGroup ™ automated blood typing system automatically supplies a possible value, such as today's date. This is called a default value, and it essentially represents an educated guess that this value will be correct. Usually the default setting will be appropriate, but if it isn't, the user simply types over it. To create a blank, the user presses the space bar. When the setting is correct, the user presses Return.

Making Corrections

If the user makes an error when typing in or changing information, use the BackSpace key. This key moves the cursor to the left and deletes the character that had occupied that position. Once the user has backed up far enough to erase the error, simply enter the correct information.

In most cases, the user presses the Return key after each entry. This means that the user can make as many changes as wanted before pressing Return: the host computer 20 will only act on the final version on your input.

In some situations, when the user is supplying a series of values, the cursor automatically moves to the next data entry position after the user completes the current entry. Here the user only presses Return after the additions or changes to the entire screen are complete. If the user finds an error before pressing the Return key use the arrow keys to move the cursor back to the location that needs correction.

If the user doesn't notice a mistake until after the user has pressed the Return key, the solution is to choose the "Return to This Screen" option on the horizontal menu at the bottom of the screen. This option returns you to the data portion of the screen, so the user can make whatever changes are necessary. If the program has already advanced to the next screen, the user can usually select the option called "Return to Previous Screen". This achieves the same object: placing the user again at the top of the screen where the correction is needed.

Moving the Cursor

Screen Types

The way the user moves the cursor around the screen depends on the type of screen the user is working with. The host computer 20 uses field screen and scrolled screens.

Field Screens

If a single screen can present all the pertinent information in a single display, the screen is called a "field". Here the user moves the cursor around using just the right and left arrow keys, as one would do within a menu. The right arrow moves the cursor to the right or down, and the left arrow moves the cursor to the left or up.

Scrolled Screens

Other screens include more data than can be presented in a single display. These screens are called scrolled screens, and they are identified by a bold band at the top and bottom of the data area. An example is shown below. Here, the complete screen contains a predetermined number of lines of data and the display can only present a few lines at a time. On scrolled screens the user uses the up and down arrow keys to move the cursor from one line to the next, and to essentially pull the data up or push it down so that a different portion will be visible in the display. Here again, the right and left arrows move the cursor horizontally, but for vertical movements the user uses the up and down arrows.

Composite Screens

Many screens that solicit or present data include a horizontal menu of options. These screens are essentially a composite of a field or a scrolled area and a menu line.

If, as shown above, the screen contains a field area, the cursor will automatically move to the first menu selection after the user supplies any data that is required.

If the screen contains a scrolled area, as shown below, the user must press Return to move the cursor from the data area to the menu area.

Other On-Screen Information

Status And Error Messages

A single line at the bottom of the screen is reserved for error messages, and for information about the host computer 20's activities. For example, if the user selects the function results summary 190 in FIG. 3 and display of WBN test results 202 in FIG. 8, the headings for the table appear on the screen first, then the menu line is displayed. Then there is a short pause and the status line provides the message "Reading In Data". A few seconds later, the stored data is incorporated into the screen image, and the status message disappears.

Error messages are presented in English, and the error message disappears a short time later.

System Security

ProGroup TM automated blood typing system has a security arrangement that prevents unauthorized access to system functions. When the ProGroup TM automated blood typing system system is installed in a blood bank laboratory, one individual assumes the responsibility of acting as its Director. This person creates a table of ProGroup TM automated blood typing system users, identifying each by means of their initials and a defined password, and assigning each a security level of 1, 2 or 3.

Logging On

The user logs onto the system by entering the information request. The user then types in his password, but it is not displayed on the terminal screen to maintain its confidentiality. The system matches the initials and password the user gives against the information stored in the user privilege table that is set up by the system director. The system director sets up the user privilege table by selecting option 300 in FIG. 3 which vectors processing to the process shown in FIG. 11. Then the user selects step 302 and enters the data in the table of user ID's and system security information.

This matching of ID's to entries in the system user privilege table serves the following purposes.

Identifying Users

The user responses to the logon screen establish whether or not the user is entitled to use the system. If the user enters his initials or password incorrectly, the screen will display an error message. The system will allow retries in case of a typographical error.

The way the user logs on also defines to the ProGroup TM automated blood typing system which system functions the user is authorized to use. Certain functions, such as calibrating the plate reader, i.e., the process shown in FIG. 9, are very critical to the ProGroup TM automated blood typing system's successful operation. Consequently, only the system Director has access to this function.

If the user has inadvertently selected a function that the user is not authorized to use, the user will see an error message. The user may then pick another function.

Accountability for Work

The further purpose of the logon procedure is to make it possible to identify which user is responsible for the work the system carries out during a given interval. Only one person can be logged on to ProGroup TM automated blood typing system at a time. If the user is logged onto the system for two hours in the morning, for example, the user's initials will be printed on the laboratory data records for samples tested during that period.

Likewise, if the user is authorized to enter or edit data manually, the user's initials will be printed on the laboratory data record for any test results the user works with manually. The ProGroup TM automated blood typing system only identifies the system user who worked with the data most recently, however. Consequently, if the user changes a given test result, and another system user changes these same results again later, their initials will replace the user's on the data record.

Thus, the logon procedure enhances the security of the blood bank operation by limiting access to the system as a whole, and to crucial functions in particular, and by increasing the accountability for work performed using the system.

Storing Information On The System Manager

Storing Data On Disk

The fixed disk can hold 10 Mbytes of data, and it is permanently resident in the computer. The floppy disks hold 360 Kbytes of data, and these are interchangeable. The user can format disks in preparation for storage on them by selecting option 400 on FIG. 3 which vectors processing to the process shown on FIG. 10. The user can then select option 402 and format the floppy diskette. The user inserts a floppy disk in the drive when the user wants to use the information it contains, and the user removes the floppy disk when the user is finished with its contents. Step 404 in FIG. 10 allows the user to transfer completed results onto the hard disk. Option 406 allows the user to back up data on the hard disk to a floppy diskette. Option 408 allows the user to reset data for a specified WBN or plate, while option 410 allows the user to delete data by any of the criteria specified in options 411–414. Data statistics can be displayed by selecting option 416.

The fixed disk offers much faster access to data, as well as greater ease of use. For this reason, the fixed disk is used for primary storage of programs and data. The floppy disks are primarily used to backup information, to facilitate recovery in the event of a problem with the hard disk, and to archive data that is no longer actively needed on the hard disk.

Working With The ProGroup Automated Blood Typing System Disks

The only ProGroup TM automated blood typing system user who is directly involved with the fixed disk and floppy disk drives is the system Supervisor. This person has a range of important responsibilities for information storage which are summarized below. The Supervisor performs the following ProGroup TM automated blood typing system functions.

Keeps track of how much data is stored on the fixed disk. This is important because the fixed disk must always have enough space for the data that will be generated in the course of the day.

Transfers test results to the blood bank mainframe computer on a regular basis,

Archive other important information, such as histograms, onto floppy disks for safekeeping, Delete unneeded information from the fixed disk on a regular basis.

The ProGroup TM automated blood typing system software provides convenient functions for carrying out these tasks. For information on how to handle the system floppy disks, refer to the DEC Micro PDP/11 Operation Manual. In addition, the Supervisor is responsible for developing and implementing a clear system for backup programs and data onto floppy disks, so that the contents and the generation of the disk are clearly identified.

It is claimed:

1. An apparatus for optimizing the accuracy of light absorbance readings taken by a plate reader regardless of the type of plate and type of well in said plate comprising:

means for causing the plate reader to take multiple light absorbance readings at different locations across the bottom of each well;

means for displaying the absorbance readings in graphical form to a user and for displaying the current locations of at least one off center absorbance reading used to discriminate positive reactions from negative reactions;

means for allowing the user to move the locations of the off center absorbance reading relative to the rest of the graphic display to optimize the discriminatory powers of the system to distinguish between positive and negative reactions; and means to record the user's choice for the position of the off center reading for use in further plate reading operations.

2. The apparatus of claim 1 wherein the means for graphically displaying the absorbance data and for allowing the user to move the position of the off center reading is a host computer and further comprising:

means for allowing the user to perform automated liquid handling on each different plate type using a sequence of liquid handling steps which is customized for that plate type;

means for reading a bar code on each plate type and for sending this data to said host system with tag data for plates which have predetermined liquid handling sequences, said tag data indicating that the plate has a well bottom geometry for which the plate reader system is not currently optimized;

means in said plate reader for reading the bar codes on plates placed therein for reading and for sending the bar code data to said host system;

means in said host system for looking up the bar code data received from the plate reader and determining whether the plate is a type for which the plate reader has not been optimized in position of the off center reading;

means for controlling the plate reader to cause said means for causing multiple absorbance readings to be taken to take said readings.

3. An apparatus in an automated blood assay system including a plate reader to allow a user to control the position at which the plate reader takes its off well bottom center light absorbance readings comprising:

means to measure light absorbance along a plurality of paths through the well bottom;

means to graphically display each absorbance versus the position relative to the well bottom center of the path to which each absorbance corresponds and to display the current path being used for the off center light absorbance reading used in the blood assay; and means for allowing the user to redefine the desired path for the off center light absorbance reading by graphically moving a pointer to the desired path position.

4. An apparatus for performing automated blood grouping on donor samples comprising:

a computer directed liquid handler means to perform predetermined automated sequences of operations involving placing aliquots of donor red blood cells and plasma into a plurality of wells in a plurality of assay trays and placing predetermined reagents in predetermined ones of said assay wells;

a computer directed plate reader to measure light absorbance data for the wells in said trays; and a host computer for sending commands to control the operations of said plate reader and said liquid handler and for collecting, analyzing and storing the light absorbance data from said plate reader to determine the blood group and type of each donor's blood, said host computer also having means therein for allowing the user to define graphically the optimum position for shining light through the bottom of one of said assay wells to measure light absorbance so as to maximize the accuracy of the host computer in determining blood group and type including means to cause said plate reader to measure the light absorbance along a plurality of different paths through the bottom of a well containing a positive reaction agglutination button and to send said data to said host computer and including means to display the light absorbance along said plurality of different light paths through said well as a graph of light absorbance versus steps off center of well bottom center for each said path and including means for graphically displaying the current position for at least one off well bottom center light absorbance reading used for measuring light absorbance in automated blood assay and for allowing the user to graphically alter the position at which this off well bottom center light absorbance reading is taken by moving the marker on the light absorbance graph.

5. The apparatus of claim 4 further comprising:

means in said liquid handler to read the bar codes of test tubes containing donor samples and the bar codes of trays into which the donor samples are deposited and for sending this data to the host computer for storage in a look up table and further comprising means for appending either a steps off center code or a histogram code to bar codes for trays whose light absorbance data is to be graphically displayed to the user;

means in said plate reader for detecting these histogram or steps off center codes and for sending same to said host computer along with light absorbance data from each well in each tray along with data labelling the light absorbance data for each well from each tray with identifying information locating the well and tray from which the data came; and means in said host computer for storing and analyzing the data from the plate reader to determine the blood group and type of each user including means for processing the data from each well in which the same type reagent was placed into histogram format and for graphically displaying same to the user along with the absorbance values currently set as the positive and negative reaction discrimination thresholds and for allowing the user to graphically adjust the positions and absorbance values for said thresholds.

6. The apparatus of claim 5 further comprising means in said host computer for allowing the user to put a known blood group and type into the liquid handler and for displaying the known reaction template for that known blood group and type on a display and for using the new thresholds to experimentally determine a reaction template for reactions to all the conventional reagents used in blood typing and for displaying the experimentally determined reaction template on the same display with the known template for that blood group and type for comparison by the user.

7. The apparatus of claim 6 further comprising means in said host computer for allowing the user to change the thresholds on the histograms until the number of no type determined donor samples or the matching between the known templates and the experimentally determined templates using the new thresholds is acceptable.

* * * * *